(12) United States Patent
Jackson

(10) Patent No.: US 8,092,500 B2
(45) Date of Patent: Jan. 10, 2012

(54) DYNAMIC STABILIZATION CONNECTING MEMBER WITH FLOATING CORE, COMPRESSION SPACER AND OVER-MOLD

(76) Inventor: Roger P. Jackson, Prairie Village, KS (US)

( * ) Notice: Subject to any disclaimer, the term of this patent is extended or adjusted under 35 U.S.C. 154(b) by 147 days.

(21) Appl. No.: 12/584,981

(22) Filed: Sep. 15, 2009

(65) Prior Publication Data

US 2010/0010543 A1    Jan. 14, 2010

Related U.S. Application Data

(63) Continuation-in-part of application No. 12/459,492, filed on Jul. 1, 2009, and a continuation-in-part of application No. 12/287,035, filed on Oct. 3, 2008, and a continuation-in-part of application No. 12/156,260, filed on May 30, 2008, and a continuation-in-part of application No. 12/148,465, filed on Apr. 18, 2008.

(60) Provisional application No. 61/201,806, filed on Dec. 15, 2008, provisional application No. 61/134,480, filed on Jul. 10, 2008, provisional application No. 61/137,743, filed on Aug. 1, 2008, provisional application No. 60/999,965, filed on Oct. 23, 2007, provisional application No. 60/932,567, filed on May 31, 2007, provisional application No. 60/994,068, filed on Sep. 17, 2007, provisional application No. 60/927,111, filed on May 1, 2007.

(51) Int. Cl.
*A61B 17/70* (2006.01)

(52) U.S. Cl. .................. 606/254; 606/246; 606/264

(58) Field of Classification Search .................. 606/246, 606/279, 301, 308, 86 A, 86 B, 264, 254
See application file for complete search history.

(56) References Cited

U.S. PATENT DOCUMENTS

| | | | |
|---|---|---|---|
| 2,243,717 A | 5/1941 | Moreira |
| 3,236,275 A | 2/1966 | Smith |
| 3,604,487 A | 9/1971 | Gilbert |
| 3,640,416 A | 2/1972 | Temple |
| 4,041,939 A | 8/1977 | Hall |
| 4,373,754 A | 2/1983 | Bollfrass et al. |
| 4,448,191 A | 5/1984 | Rodnyansky et al. |
| 4,484,570 A | 11/1984 | Sutter et al. |
| 4,600,224 A | 7/1986 | Blose |
| 4,653,486 A | 3/1987 | Coker |

(Continued)

FOREIGN PATENT DOCUMENTS

DE    G9202745.8    4/1992

(Continued)

OTHER PUBLICATIONS

*EBI Omega 21* Brochure, EBI Spine Systems, pub. 1999.

(Continued)

*Primary Examiner* — Pedro Philogene
(74) *Attorney, Agent, or Firm* — John C. McMahon

(57) ABSTRACT

A dynamic fixation medical implant having at least two bone anchors includes a dynamic longitudinal connecting member assembly having the following features: a pair of elongate bone anchor engagement segments, a floating inner core disposed in apertures of both anchor segments, at least one compression spacer surrounding the core and located between the anchor segments and in some embodiments an over-mold surrounding the compression spacer and at least a portion of one of the anchor segments. The implant may further include a tubed sleeve surrounding the core and located between the anchor segments.

28 Claims, 12 Drawing Sheets

U.S. PATENT DOCUMENTS

| | | |
|---|---|---|
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,836,196 A | 6/1989 | Park et al. |
| 4,887,596 A | 12/1989 | Sherman |
| 4,946,458 A | 8/1990 | Harms et al. |
| 4,950,269 A | 8/1990 | Gaines, Jr. |
| 5,005,562 A | 4/1991 | Cotrel |
| 5,022,791 A | 6/1991 | Isler |
| 5,034,011 A | 7/1991 | Howland |
| 5,067,955 A | 11/1991 | Cotrel |
| 5,092,635 A | 3/1992 | DeLange et al. |
| 5,102,412 A | 4/1992 | Rogozinski |
| 5,129,388 A | 7/1992 | Vignaud et al. |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,680 A | 1/1993 | Vignaud et al. |
| 5,180,393 A | 1/1993 | Commarmond |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,261,912 A | 11/1993 | Frigg |
| 5,275,601 A | 1/1994 | Gogolewski et al. |
| 5,282,863 A | 2/1994 | Burton |
| 5,306,275 A | 4/1994 | Bryan |
| 5,312,404 A | 5/1994 | Asher et al. |
| 5,321,901 A | 6/1994 | Kelly |
| 5,346,493 A | 9/1994 | Stahurski et al. |
| 5,358,289 A | 10/1994 | Banker et al. |
| 5,360,431 A | 11/1994 | Puno et al. |
| 5,375,823 A | 12/1994 | Navas |
| 5,385,583 A | 1/1995 | Cotrel |
| 5,395,371 A | 3/1995 | Miller et al. |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,468,241 A | 11/1995 | Metz-Stavenhagen et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,487,742 A | 1/1996 | Cotrel |
| 5,489,307 A | 2/1996 | Kuslich et al. |
| 5,490,750 A | 2/1996 | Gundy |
| 5,496,321 A | 3/1996 | Puno |
| 5,499,892 A | 3/1996 | Reed |
| 5,507,745 A | 4/1996 | Logroscino et al. |
| 5,540,688 A | 7/1996 | Navas |
| 5,545,165 A | 8/1996 | Biedermann et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,662,652 A | 9/1997 | Schafer et al. |
| 5,662,653 A | 9/1997 | Songer et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann et al. |
| 5,681,319 A | 10/1997 | Biedermann et al. |
| 5,683,390 A | 11/1997 | Metz-Stavenhagen et al. |
| 5,690,630 A | 11/1997 | Errico et al. |
| 5,697,929 A | 12/1997 | Mellinger |
| 5,711,709 A | 1/1998 | McCoy |
| 5,713,898 A | 2/1998 | Stucker et al. |
| 5,716,356 A | 2/1998 | Biedermann et al. |
| 5,723,013 A | 3/1998 | Jeanson et al. |
| 5,725,527 A | 3/1998 | Biedermann et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,833 A | 7/1998 | Haider |
| 5,797,911 A | 8/1998 | Sherman et al. |
| 5,800,435 A | 9/1998 | Errico et al. |
| 5,800,547 A | 9/1998 | Schafer et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| RE36,221 E | 6/1999 | Breard et al. |
| 5,944,465 A | 8/1999 | Janitzki |
| 5,951,553 A | 9/1999 | Betz |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,913 A | 8/2000 | Jackson |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,136,002 A | 10/2000 | Shih et al. |
| 6,143,032 A | 11/2000 | Schafer et al. |
| 6,146,383 A | 11/2000 | Studer et al. |
| 6,183,472 B1 | 2/2001 | Lutz |
| RE37,161 E | 5/2001 | Michelson et al. |
| 6,224,596 B1 | 5/2001 | Jackson |
| 6,224,598 B1 | 5/2001 | Jackson |
| 6,235,034 B1 | 5/2001 | Bray |
| 6,241,730 B1 * | 6/2001 | Alby .............................. 606/256 |
| 6,248,105 B1 | 6/2001 | Schlapfer et al. |
| 6,254,146 B1 | 7/2001 | Church |
| 6,254,602 B1 | 7/2001 | Justis |
| 6,267,764 B1 | 7/2001 | Elberg |
| 6,267,765 B1 | 7/2001 | Taylor et al. |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,302,888 B1 | 10/2001 | Mellinger et al. |
| 6,309,391 B1 | 10/2001 | Crandall et al. |
| 6,315,564 B1 | 11/2001 | Levisman |
| 6,331,179 B1 | 12/2001 | Freid et al. |

| | | |
|---|---|---|
| 6,355,040 B1 | 3/2002 | Richelsoph et al. |
| RE37,665 E | 4/2002 | Ralph et al. |
| 6,368,321 B1 | 4/2002 | Jackson |
| 6,402,752 B2 | 6/2002 | Schaffler-Wachter et al. |
| 6,402,757 B1 | 6/2002 | Moore et al. |
| 6,440,137 B1 | 8/2002 | Horvath et al. |
| 6,451,021 B1 | 9/2002 | Ralph et al. |
| 6,471,703 B1 | 10/2002 | Ashman |
| 6,471,705 B1 | 10/2002 | Biedermann et al. |
| 6,485,491 B1 | 11/2002 | Farris et al. |
| 6,485,492 B1 | 11/2002 | Halm et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,527,804 B2 | 3/2003 | Gauchet et al. |
| 6,530,929 B1 | 3/2003 | Justis et al. |
| 6,533,786 B1 | 3/2003 | Needham et al. |
| 6,540,749 B2 | 4/2003 | Schafer et al. |
| 6,547,790 B2 | 4/2003 | Harkey, III et al. |
| 6,551,320 B2 | 4/2003 | Lieberman |
| 6,551,323 B2 | 4/2003 | Doubler et al. |
| 6,554,831 B1 | 4/2003 | Rivard et al. |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,648,885 B1 | 11/2003 | Friesem |
| 6,648,887 B2 | 11/2003 | Ashman |
| 6,652,765 B1 | 11/2003 | Beaty |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Martin Benlloch et al. |
| 6,679,833 B2 | 1/2004 | Smith et al. |
| 6,682,529 B2 | 1/2004 | Stahurski |
| 6,682,530 B2 | 1/2004 | Dixon et al. |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,783,527 B2 | 8/2004 | Drewry et al. |
| 6,790,209 B2 | 9/2004 | Beale et al. |
| 6,802,844 B2 | 10/2004 | Ferree |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,837,889 B2 | 1/2005 | Shluzas |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,676 B2 | 5/2005 | Zubok et al. |
| 6,932,817 B2 | 8/2005 | Baynham et al. |
| 6,932,820 B2 | 8/2005 | Osman |
| 6,945,972 B2 | 9/2005 | Frigg et al. |
| 6,953,462 B2 | 10/2005 | Liebermann |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |
| RE39,035 E | 3/2006 | Finn et al. |
| 7,008,424 B2 | 3/2006 | Teitelbaum |
| 7,018,378 B2 | 3/2006 | Biedermann et al. |
| 7,018,379 B2 | 3/2006 | Drewry et al. |
| 7,029,475 B2 | 4/2006 | Panjabi |
| 7,125,410 B2 | 10/2006 | Freudiger |
| 7,137,985 B2 | 11/2006 | Jahng |
| 7,207,992 B2 | 4/2007 | Ritland |
| 7,229,441 B2 | 6/2007 | Trieu et al. |
| 7,294,129 B2 | 11/2007 | Hawkins et al. |
| 7,329,258 B2 | 2/2008 | Studer |
| 7,361,196 B2 | 4/2008 | Fallin et al. |
| 7,377,921 B2 | 5/2008 | Studer et al. |
| 7,476,238 B2 | 1/2009 | Panjabi |
| 7,556,639 B2 | 7/2009 | Rothman et al. |
| 7,559,942 B2 | 7/2009 | Paul et al. |
| 7,563,274 B2 | 7/2009 | Justis et al. |
| 7,563,283 B2 | 7/2009 | Kwak |
| 7,763,048 B2 * | 7/2010 | Fortin et al. .................. 606/246 |
| 7,815,665 B2 * | 10/2010 | Jahng et al. ................... 606/263 |
| 7,828,823 B2 * | 11/2010 | Rogeau et al. ................ 606/256 |
| 7,842,072 B2 * | 11/2010 | Dawson ........................ 606/263 |
| 2001/0001119 A1 | 5/2001 | Lombardo |
| 2001/0010000 A1 | 7/2001 | Gertzbein |
| 2001/0029375 A1 | 10/2001 | Betz |
| 2001/0037111 A1 | 11/2001 | Dixon et al. |
| 2002/0007184 A1 | 1/2002 | Ogilvie et al. |
| 2002/0013586 A1 | 1/2002 | Justis et al. |
| 2002/0035366 A1 | 3/2002 | Walder et al. |
| 2002/0045898 A1 | 4/2002 | Freid et al. |
| 2002/0058942 A1 | 5/2002 | Biedermann et al. |
| 2002/0082602 A1 | 6/2002 | Biedermann et al. |
| 2002/0111626 A1 | 8/2002 | Ralph et al. |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0023243 A1 | 1/2003 | Biedermann et al. |
| 2003/0073996 A1 | 4/2003 | Doubler et al. |
| 2003/0083657 A1 | 5/2003 | Drewry et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125741 A1 | 7/2003 | Biedermann et al. |
| 2003/0149432 A1 | 8/2003 | Frigg et al. |
| 2003/0163133 A1 | 8/2003 | Altarac et al. |
| 2003/0171749 A1 | 9/2003 | Le Couedic et al. |
| 2003/0176862 A1 | 9/2003 | Taylor et al. |
| 2003/0191470 A1 | 10/2003 | Ritland |
| 2003/0199873 A1 | 10/2003 | Richelsoph |

| | | | | | | |
|---|---|---|---|---|---|---|
| 2003/0208204 A1 | 11/2003 | Bailey et al. | | 2005/0234451 A1 | 10/2005 | Markworth |
| 2003/0216735 A1 | 11/2003 | Altarac et al. | | 2005/0234452 A1 | 10/2005 | Malandain |
| 2003/0220642 A1 | 11/2003 | Freudiger | | 2005/0234453 A1 | 10/2005 | Shaolian et al. |
| 2003/0220643 A1 | 11/2003 | Ferree | | 2005/0234454 A1 | 10/2005 | Chin |
| 2004/0002708 A1 | 1/2004 | Ritland | | 2005/0234456 A1 | 10/2005 | Malandain |
| 2004/0006342 A1 | 1/2004 | Altarac et al. | | 2005/0240181 A1 | 10/2005 | Boomer et al. |
| 2004/0049189 A1 | 3/2004 | Le Couedic et al. | | 2005/0240183 A1 | 10/2005 | Vaughan |
| 2004/0049190 A1 | 3/2004 | Biedermann et al. | | 2005/0245930 A1 | 11/2005 | Timm et al. |
| 2004/0073215 A1 | 4/2004 | Carli | | 2005/0251137 A1 | 11/2005 | Ball |
| 2004/0078082 A1 | 4/2004 | Lange | | 2005/0251140 A1 | 11/2005 | Shaolian et al. |
| 2004/0087949 A1 | 5/2004 | Bono et al. | | 2005/0251141 A1 | 11/2005 | Frigg et al. |
| 2004/0087952 A1 | 5/2004 | Borgstrom et al. | | 2005/0261685 A1 | 11/2005 | Fortin et al. |
| 2004/0092934 A1 | 5/2004 | Howland | | 2005/0261687 A1 | 11/2005 | Garamszegi et al. |
| 2004/0097933 A1 | 5/2004 | Lourdel et al. | | 2005/0267470 A1 | 12/2005 | McBride |
| 2004/0116929 A1 | 6/2004 | Barker et al. | | 2005/0267471 A1 | 12/2005 | Biedermann et al. |
| 2004/0138662 A1 | 7/2004 | Landry et al. | | 2005/0267474 A1 | 12/2005 | Dalton |
| 2004/0143265 A1 | 7/2004 | Landry et al. | | 2005/0273099 A1 | 12/2005 | Baccelli et al. |
| 2004/0147928 A1 | 7/2004 | Landry et al. | | 2005/0273101 A1 | 12/2005 | Schumacher |
| 2004/0147929 A1 | 7/2004 | Biedermann et al. | | 2005/0277919 A1 | 12/2005 | Slivka et al. |
| 2004/0158247 A1 | 8/2004 | Sitiso et al. | | 2005/0277922 A1 | 12/2005 | Trieu et al. |
| 2004/0172022 A1 | 9/2004 | Landry et al. | | 2005/0277923 A1 | 12/2005 | Sweeney |
| 2004/0176766 A1 | 9/2004 | Shluzas | | 2005/0277925 A1 | 12/2005 | Mujwid |
| 2004/0186473 A1 | 9/2004 | Cournoyer et al. | | 2005/0277927 A1 | 12/2005 | Guenther et al. |
| 2004/0210216 A1 | 10/2004 | Farris et al. | | 2005/0277928 A1 | 12/2005 | Boschert |
| 2004/0225289 A1 | 11/2004 | Biedermann et al. | | 2005/0283152 A1 | 12/2005 | Lindemann et al. |
| 2004/0236327 A1 | 11/2004 | Paul et al. | | 2005/0283157 A1 | 12/2005 | Coates et al. |
| 2004/0236328 A1 | 11/2004 | Paul et al. | | 2005/0283238 A1 | 12/2005 | Reiley |
| 2004/0236329 A1 | 11/2004 | Panjabi | | 2005/0283244 A1 | 12/2005 | Gordon et al. |
| 2004/0236330 A1 | 11/2004 | Purcell et al. | | 2005/0288669 A1 | 12/2005 | Abdou |
| 2004/0249380 A1 | 12/2004 | Glascott | | 2005/0288670 A1 | 12/2005 | Panjabi et al. |
| 2004/0260283 A1 | 12/2004 | Wu et al. | | 2005/0288671 A1 | 12/2005 | Yuan et al. |
| 2004/0267264 A1 | 12/2004 | Konieczynski et al. | | 2005/0288672 A1 | 12/2005 | Ferree |
| 2005/0027296 A1 | 2/2005 | Thramann et al. | | 2005/0288673 A1 | 12/2005 | Catbagan et al. |
| 2005/0033298 A1 | 2/2005 | Hawkes et al. | | 2006/0004357 A1 | 1/2006 | Lee et al. |
| 2005/0038432 A1 | 2/2005 | Shaolian et al. | | 2006/0004359 A1 | 1/2006 | Kramer et al. |
| 2005/0049708 A1 | 3/2005 | Atkinson et al. | | 2006/0004360 A1 | 1/2006 | Kramer et al. |
| 2005/0055026 A1 | 3/2005 | Biedermann et al. | | 2006/0004363 A1 | 1/2006 | Brockmeyer et al. |
| 2005/0065515 A1 | 3/2005 | Jahng | | 2006/0009767 A1 | 1/2006 | Kiester |
| 2005/0065516 A1 | 3/2005 | Johng | | 2006/0009768 A1 | 1/2006 | Ritland |
| 2005/0070899 A1 | 3/2005 | Doubler et al. | | 2006/0009769 A1 | 1/2006 | Liebermann |
| 2005/0080415 A1 | 4/2005 | Keyer et al. | | 2006/0009770 A1 | 1/2006 | Speirs et al. |
| 2005/0085815 A1 | 4/2005 | Harms et al. | | 2006/0009846 A1 | 1/2006 | Trieu et al. |
| 2005/0085816 A1 | 4/2005 | Michelson | | 2006/0015099 A1 | 1/2006 | Cannon et al. |
| 2005/0096652 A1 | 5/2005 | Burton | | 2006/0015104 A1 | 1/2006 | Dalton |
| 2005/0107788 A1 | 5/2005 | Beaurain et al. | | 2006/0025767 A1 | 2/2006 | Khalili |
| 2005/0113927 A1 | 5/2005 | Malek | | 2006/0025768 A1 | 2/2006 | Iott et al. |
| 2005/0124991 A1 | 6/2005 | Jahng | | 2006/0025770 A1 | 2/2006 | Schlapfer et al. |
| 2005/0131404 A1 | 6/2005 | Mazda et al. | | 2006/0036240 A1 | 2/2006 | Colleran et al. |
| 2005/0131407 A1 | 6/2005 | Sicvol et al. | | 2006/0036242 A1 | 2/2006 | Nilsson et al. |
| 2005/0131413 A1 | 6/2005 | O'Driscoll et al. | | 2006/0036244 A1 | 2/2006 | Spitler et al. |
| 2005/0137597 A1 | 6/2005 | Butler et al. | | 2006/0036246 A1 | 2/2006 | Carl et al. |
| 2005/0143737 A1 | 6/2005 | Pafford et al. | | 2006/0036252 A1 | 2/2006 | Baynham et al. |
| 2005/0143823 A1 | 6/2005 | Boyd et al. | | 2006/0036256 A1 | 2/2006 | Carl et al. |
| 2005/0149020 A1 | 7/2005 | Jahng | | 2006/0036259 A1 | 2/2006 | Carl et al. |
| 2005/0149023 A1 | 7/2005 | Ritland | | 2006/0036323 A1 | 2/2006 | Carl et al. |
| 2005/0154389 A1 | 7/2005 | Selover et al. | | 2006/0036324 A1 | 2/2006 | Sachs et al. |
| 2005/0154390 A1 | 7/2005 | Biedermann et al. | | 2006/0041259 A1 | 2/2006 | Paul et al. |
| 2005/0154391 A1 | 7/2005 | Doherty et al. | | 2006/0052780 A1 | 3/2006 | Errico et al. |
| 2005/0159750 A1 | 7/2005 | Doherty | | 2006/0052783 A1 | 3/2006 | Dant et al. |
| 2005/0165396 A1 | 7/2005 | Fortin et al. | | 2006/0052784 A1 | 3/2006 | Dant et al. |
| 2005/0165400 A1 | 7/2005 | Fernandez | | 2006/0052786 A1 | 3/2006 | Dant et al. |
| 2005/0171540 A1 | 8/2005 | Lim et al. | | 2006/0058788 A1 | 3/2006 | Hammer et al. |
| 2005/0171543 A1 | 8/2005 | Timm et al. | | 2006/0058790 A1 | 3/2006 | Carl et al. |
| 2005/0177157 A1 | 8/2005 | Jahng | | 2006/0064090 A1 | 3/2006 | Park |
| 2005/0182401 A1 | 8/2005 | Timm et al. | | 2006/0064091 A1 | 3/2006 | Ludwig et al. |
| 2005/0187548 A1 | 8/2005 | Butler et al. | | 2006/0064092 A1 | 3/2006 | Howland |
| 2005/0187555 A1 | 8/2005 | Biedermann et al. | | 2006/0069390 A1 | 3/2006 | Frigg |
| 2005/0192580 A1 | 9/2005 | Dalton | | 2006/0079896 A1 | 4/2006 | Kwak |
| 2005/0203511 A1 | 9/2005 | Wilson-MacDonald et al. | | 2006/0079898 A1 | 4/2006 | Ainsworth |
| 2005/0203513 A1 | 9/2005 | Jahng et al. | | 2006/0084982 A1 | 4/2006 | Kim |
| 2005/0203514 A1 | 9/2005 | Jahng et al. | | 2006/0084983 A1 | 4/2006 | Kim |
| 2005/0203516 A1 | 9/2005 | Biedermann et al. | | 2006/0084984 A1 | 4/2006 | Kim |
| 2005/0203517 A1 | 9/2005 | Jahng et al. | | 2006/0084985 A1 | 4/2006 | Kim |
| 2005/0203518 A1 | 9/2005 | Biedermann et al. | | 2006/0084987 A1 | 4/2006 | Kim |
| 2005/0203519 A1 | 9/2005 | Harms et al. | | 2006/0084988 A1 | 4/2006 | Kim |
| 2005/0216001 A1 | 9/2005 | David | | 2006/0084991 A1 | 4/2006 | Borgstrom |
| 2005/0216003 A1 | 9/2005 | Biedermann et al. | | 2006/0085069 A1 | 4/2006 | Kim |
| 2005/0228501 A1 | 10/2005 | Miller et al. | | 2006/0106381 A1 | 5/2006 | Ferree |
| 2005/0234450 A1 | 10/2005 | Barker | | 2006/0122599 A1 | 6/2006 | Drewry |

| | | | | | | |
|---|---|---|---|---|---|---|
| 2006/0129239 A1 | 6/2006 | Kwak | | 2007/0270814 A1 | 11/2007 | Lim et al. |
| 2006/0142758 A1 | 6/2006 | Petit | | 2007/0270837 A1 | 11/2007 | Eckhardt et al. |
| 2006/0142760 A1 | 6/2006 | McDonnell | | 2007/0270838 A1 | 11/2007 | Bruneau et al. |
| 2006/0149228 A1 | 7/2006 | Schlapfer | | 2007/0270843 A1 | 11/2007 | Matthis et al. |
| 2006/0149229 A1 | 7/2006 | Kwak | | 2007/0276380 A1 | 11/2007 | Jahng et al. |
| 2006/0184171 A1 | 8/2006 | Biedermann | | 2007/0288008 A1 | 12/2007 | Park |
| 2006/0184180 A1 | 8/2006 | Augostino | | 2007/0288009 A1 | 12/2007 | Brown et al. |
| 2006/0189983 A1 | 8/2006 | Fallin | | 2007/0288011 A1 | 12/2007 | Logan |
| 2006/0189984 A1 | 8/2006 | Fallin | | 2007/0288012 A1 | 12/2007 | Colleran et al. |
| 2006/0189985 A1 | 8/2006 | Lewis | | 2008/0021458 A1 | 1/2008 | Lim |
| 2006/0195090 A1 | 8/2006 | Suddaby | | 2008/0021459 A1 | 1/2008 | Lim |
| 2006/0195093 A1 | 8/2006 | Jahng | | 2008/0021462 A1 | 1/2008 | Trieu |
| 2006/0200130 A1 | 9/2006 | Hawkins | | 2008/0021464 A1 | 1/2008 | Norin et al. |
| 2006/0212033 A1 | 9/2006 | Rothman | | 2008/0021465 A1 | 1/2008 | Shadduck et al. |
| 2006/0229608 A1 | 10/2006 | Foster | | 2008/0021466 A1 | 1/2008 | Shadduck et al. |
| 2006/0229609 A1 | 10/2006 | Wang | | 2008/0033435 A1 | 2/2008 | Studer et al. |
| 2006/0229612 A1 | 10/2006 | Rothman | | 2008/0039843 A1 | 2/2008 | Abdou |
| 2006/0229613 A1 | 10/2006 | Timm | | 2008/0045951 A1 | 2/2008 | Fanger et al. |
| 2006/0241769 A1 | 10/2006 | Gordon | | 2008/0051787 A1 | 2/2008 | Remington et al. |
| 2006/0241771 A1 | 10/2006 | Gordon | | 2008/0058812 A1 | 3/2008 | Zehnder |
| 2006/0247632 A1 | 11/2006 | Winslow | | 2008/0065071 A1 | 3/2008 | Park |
| 2006/0247633 A1 | 11/2006 | Winslow | | 2008/0065073 A1 | 3/2008 | Perriello et al. |
| 2006/0247635 A1 | 11/2006 | Gordon | | 2008/0065077 A1 | 3/2008 | Ferree |
| 2006/0247637 A1 | 11/2006 | Colleran | | 2008/0065079 A1 | 3/2008 | Bruneau et al. |
| 2006/0247779 A1 | 11/2006 | Gordon | | 2008/0071273 A1 | 3/2008 | Hawkes et al. |
| 2006/0264935 A1 | 11/2006 | White | | 2008/0071274 A1 | 3/2008 | Ensign |
| 2006/0264937 A1 | 11/2006 | White | | 2008/0091214 A1 | 4/2008 | Richelsoph |
| 2006/0264940 A1 | 11/2006 | Hartmannt | | 2008/0097431 A1 | 4/2008 | Vessa |
| 2006/0282075 A1 | 12/2006 | Labrom | | 2008/0097434 A1 | 4/2008 | Moumene et al. |
| 2006/0282076 A1 | 12/2006 | Labrom | | 2008/0097441 A1 | 4/2008 | Hayes et al. |
| 2006/0282077 A1 | 12/2006 | Labrom | | 2008/0125777 A1 | 5/2008 | Veldman et al. |
| 2006/0282078 A1 | 12/2006 | Labrom | | 2008/0125787 A1 | 5/2008 | Doubler et al. |
| 2006/0282079 A1 | 12/2006 | Labrom | | 2008/0140133 A1 | 6/2008 | Allard et al. |
| 2006/0282080 A1 | 12/2006 | Albert | | 2008/0154307 A1 | 6/2008 | Colleran et al. |
| 2006/0293657 A1 | 12/2006 | Hartmann | | 2008/0161854 A1 | 7/2008 | Bae et al. |
| 2006/0293663 A1 | 12/2006 | Walkenhorst | | 2008/0167687 A1 | 7/2008 | Colleran et al. |
| 2007/0005062 A1 | 1/2007 | Lange | | 2008/0177316 A1 | 7/2008 | Bergeron et al. |
| 2007/0005063 A1 | 1/2007 | Bruneau | | 2008/0177319 A1 | 7/2008 | Schwab |
| 2007/0005137 A1 | 1/2007 | Kwak | | 2008/0177327 A1 | 7/2008 | Malandain et al. |
| 2007/0016190 A1 | 1/2007 | Martinez | | 2008/0183212 A1 | 7/2008 | Veldman et al. |
| 2007/0016193 A1 | 1/2007 | Ritland | | 2008/0183213 A1 | 7/2008 | Veldman et al. |
| 2007/0043356 A1 | 2/2007 | Timm | | 2008/0183215 A1 | 7/2008 | Altarac et al. |
| 2007/0049936 A1 | 3/2007 | Colleran | | 2008/0183216 A1 | 7/2008 | Jackson |
| 2007/0055236 A1 | 3/2007 | Hudgins | | 2008/0183219 A1 | 7/2008 | Bertram |
| 2007/0055247 A1 | 3/2007 | Jahng | | 2008/0195100 A1 | 8/2008 | Capote et al. |
| 2007/0073289 A1 | 3/2007 | Kwak | | 2008/0215095 A1 | 9/2008 | Biedermann et al. |
| 2007/0073293 A1 | 3/2007 | Martz | | 2008/0221620 A1 | 9/2008 | Krause |
| 2007/0078461 A1 | 4/2007 | Shluzas | | 2008/0228227 A1 | 9/2008 | Brown et al. |
| 2007/0088359 A1 | 4/2007 | Woods et al. | | 2008/0228229 A1 | 9/2008 | Walder et al. |
| 2007/0093813 A1 | 4/2007 | Callahan, II et al. | | 2008/0234691 A1 | 9/2008 | Schwab |
| 2007/0093814 A1 | 4/2007 | Callahan, II et al. | | 2008/0234734 A1 | 9/2008 | Wabler et al. |
| 2007/0093815 A1 | 4/2007 | Callahan, II et al. | | 2008/0234736 A1 | 9/2008 | Trieu et al. |
| 2007/0100341 A1 | 5/2007 | Reglos et al. | | 2008/0234737 A1 | 9/2008 | Boschert |
| 2007/0118119 A1 | 5/2007 | Hestad | | 2008/0234739 A1 | 9/2008 | Hudgins et al. |
| 2007/0118122 A1 | 5/2007 | Butler et al. | | 2008/0234744 A1 | 9/2008 | Zylber et al. |
| 2007/0123864 A1 | 5/2007 | Walder et al. | | 2008/0234746 A1 | 9/2008 | Jahng et al. |
| 2007/0123865 A1 | 5/2007 | Schlapfer et al. | | 2008/0255617 A1* | 10/2008 | Cho et al. ................ 606/246 |
| 2007/0123866 A1 | 5/2007 | Gerbec et al. | | 2008/0262546 A1 | 10/2008 | Calvosa et al. |
| 2007/0123871 A1 | 5/2007 | Jahng | | 2008/0262548 A1 | 10/2008 | Lange et al. |
| 2007/0129729 A1 | 6/2007 | Petit et al. | | 2008/0262552 A1 | 10/2008 | Kim |
| 2007/0135815 A1 | 6/2007 | Gerbec et al. | | 2008/0262554 A1 | 10/2008 | Hayes et al. |
| 2007/0161991 A1 | 7/2007 | Altarac et al. | | 2008/0269804 A1 | 10/2008 | Holt |
| 2007/0161997 A1 | 7/2007 | Thramann et al. | | 2008/0275504 A1 | 11/2008 | Bonin et al. |
| 2007/0173818 A1 | 7/2007 | Hestad et al. | | 2008/0287994 A1 | 11/2008 | Perez-Cruet et al. |
| 2007/0173822 A1 | 7/2007 | Bruneau et al. | | 2008/0300630 A1 | 12/2008 | Bohnema et al. |
| 2007/0173832 A1 | 7/2007 | Tebbe et al. | | 2008/0306528 A1 | 12/2008 | Winslow et al. |
| 2007/0191841 A1 | 8/2007 | Justis et al. | | 2008/0306533 A1 | 12/2008 | Winslow et al. |
| 2007/0191846 A1 | 8/2007 | Bruneau et al. | | 2008/0306536 A1 | 12/2008 | Frigg et al. |
| 2007/0213720 A1 | 9/2007 | Gordon et al. | | 2008/0306539 A1 | 12/2008 | Cain et al. |
| 2007/0225708 A1 | 9/2007 | Biedermann et al. | | 2008/0306540 A1 | 12/2008 | Mitchell et al. |
| 2007/0225710 A1 | 9/2007 | Jahng et al. | | 2008/0306543 A1 | 12/2008 | Cain et al. |
| 2007/0233064 A1 | 10/2007 | Holt | | 2008/0306545 A1 | 12/2008 | Winslow |
| 2007/0233073 A1 | 10/2007 | Wisnewski et al. | | 2008/0312694 A1 | 12/2008 | Peterman et al. |
| 2007/0233075 A1 | 10/2007 | Dawson | | 2009/0005817 A1 | 1/2009 | Friedrich et al. |
| 2007/0233085 A1 | 10/2007 | Biedermann et al. | | 2009/0018583 A1 | 1/2009 | Song et al. |
| 2007/0233087 A1 | 10/2007 | Schlapfer | | 2009/0024165 A1 | 1/2009 | Ferree |
| 2007/0233092 A1 | 10/2007 | Falahee | | 2009/0024169 A1 | 1/2009 | Triplett et al. |
| 2007/0233094 A1 | 10/2007 | Colleran et al. | | 2009/0030464 A1 | 1/2009 | Hestad et al. |
| 2007/0233095 A1 | 10/2007 | Schlaepfer | | 2009/0030465 A1 | 1/2009 | Altarac et al. |

| Publication No. | Date | Inventor |
|---|---|---|
| 2009/0048631 A1 | 2/2009 | Bhatnagar et al. |
| 2009/0054932 A1 | 2/2009 | Butler et al. |
| 2009/0069849 A1 | 3/2009 | Oh et al. |
| 2009/0082815 A1 | 3/2009 | Zylber et al. |
| 2009/0088799 A1 | 4/2009 | Yeh |
| 2009/0088803 A1 | 4/2009 | Justis et al. |
| 2009/0093820 A1 | 4/2009 | Trieu et al. |
| 2009/0093843 A1 | 4/2009 | Lemoine et al. |
| 2009/0093845 A1 | 4/2009 | Hestad et al. |
| 2009/0093846 A1 | 4/2009 | Hestad et al. |
| 2009/0099606 A1 | 4/2009 | Hestad et al. |
| 2009/0099607 A1 | 4/2009 | Fallin et al. |
| 2009/0099608 A1 | 4/2009 | Szczesny |
| 2009/0105760 A1 | 4/2009 | Frey |
| 2009/0112265 A1 | 4/2009 | Hudgins et al. |
| 2009/0112266 A1 | 4/2009 | Weng et al. |
| 2009/0112267 A1 | 4/2009 | Atkinson et al. |
| 2009/0118767 A1 | 5/2009 | Hestad et al. |
| 2009/0125063 A1 | 5/2009 | Panjabi |
| 2009/0131981 A1 | 5/2009 | White |
| 2009/0138052 A1 | 5/2009 | Biedermann et al. |
| 2009/0149885 A1 | 6/2009 | Durward et al. |
| 2009/0163953 A1 | 6/2009 | Biedermann et al. |
| 2009/0163954 A1 | 6/2009 | Kwak |
| 2009/0163955 A1 | 6/2009 | Moumene et al. |
| 2009/0171395 A1 | 7/2009 | Jeon et al. |
| 2009/0177232 A1 | 7/2009 | Kiester |
| 2009/0192548 A1 | 7/2009 | Jeon et al. |
| 2009/0198281 A1 | 8/2009 | Rice et al. |

FOREIGN PATENT DOCUMENTS

| | | |
|---|---|---|
| DE | 4239716 | 8/1994 |
| DE | 4425392 | 11/1995 |
| DE | 19507141 | 9/1996 |
| DE | 19509331 | 9/1996 |
| DE | 29806563 | 7/1998 |
| DE | 29810798 | 12/1999 |
| DE | 19951145 | 5/2001 |
| DE | 10236691 | 2/2004 |
| DE | 102007055745 | 7/2008 |
| EP | 0667127 | 8/1995 |
| EP | 0669109 | 8/1995 |
| EP | 0677277 | 10/1995 |
| EP | 0885598 | 12/1998 |
| EP | 1121902 | 8/2001 |
| EP | 1190678 | 3/2002 |
| EP | 1570795 | 2/2005 |
| EP | 1570795 | 9/2005 |
| EP | 1579816 | 9/2005 |
| EP | 1634537 | 3/2006 |
| FR | 2717370 | 9/1995 |
| FR | 2718946 | 10/1995 |
| FR | 2729291 | 7/1996 |
| FR | 2796545 | 1/2001 |
| FR | 2799949 | 4/2001 |
| FR | 2814936 | 4/2002 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| GB | 2365345 | 2/2002 |
| GB | 2382304 | 5/2003 |
| JP | 10277070 | 10/1998 |
| JP | 2000325358 | 3/2000 |
| WO | WO92/03100 | 3/1992 |
| WO | WO94/10927 | 5/1994 |
| WO | WO94/26191 | 11/1994 |
| WO | WO9641582 | 12/1996 |
| WO | WO01/45576 | 6/2001 |
| WO | WO02/054966 | 7/2002 |
| WO | WO02/102259 | 12/2002 |
| WO | WO03/026523 | 4/2003 |
| WO | WO03/068088 | 8/2003 |
| WO | WO2004/041100 | 5/2004 |
| WO | WO2004/075778 | 9/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/065374 | 7/2005 |
| WO | WO2005/065375 | 7/2005 |
| WO | WO2005/072632 | 8/2005 |
| WO | WO2005/082262 | 9/2005 |
| WO | WO2005/099400 | 10/2005 |
| WO | WO2005/104969 | 11/2005 |
| WO | WO2006/012088 | 2/2006 |
| WO | WO2006/017616 | 2/2006 |
| WO | 2006/028537 | 3/2006 |
| WO | WO2006/045094 | 4/2006 |
| WO | WO2007/002409 | 1/2007 |
| WO | WO2007124249 | 11/2007 |
| WO | WO2008/069420 | 6/2008 |
| WO | WO2008/088990 | 7/2008 |
| WO | WO2008/089075 | 7/2008 |
| WO | WO2008/140756 | 11/2008 |
| WO | WO2009/036541 | 3/2009 |

OTHER PUBLICATIONS

*Claris Instrumentation* Brochure, G Med, pub. 1997.
*VLS System Variable Locking Screw* Brochure, Interpore Cross International, 1999.
*The Rod Plate System* Brochure, Stryker Howmedica Osteonics, pub. Oct. 1999.
*SDRS Surgical Dynamics Rod System* Brochure, Surgical Dynamics, pub. 1998-99.
*Versalok Low Back Fixation System* Brochure, Wright Medical Technology, Inc., pub. 1997.
Brochure of Tyco/Healthcare/Surgical Dynamics on Spiral Radius 90D, Publication Date: Sep. 2001, pp. 1-8.

* cited by examiner

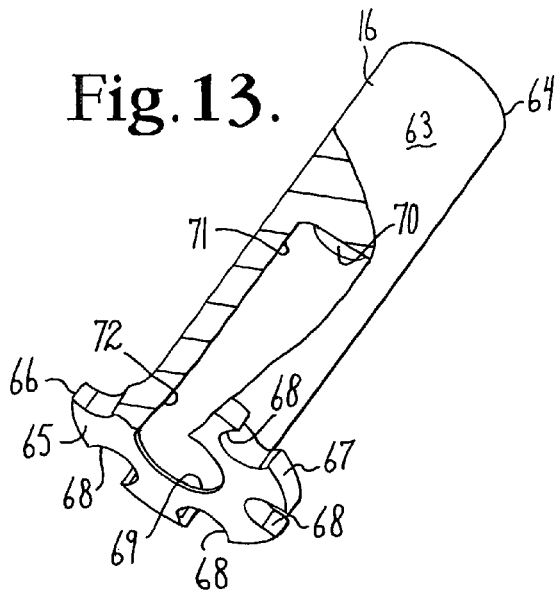
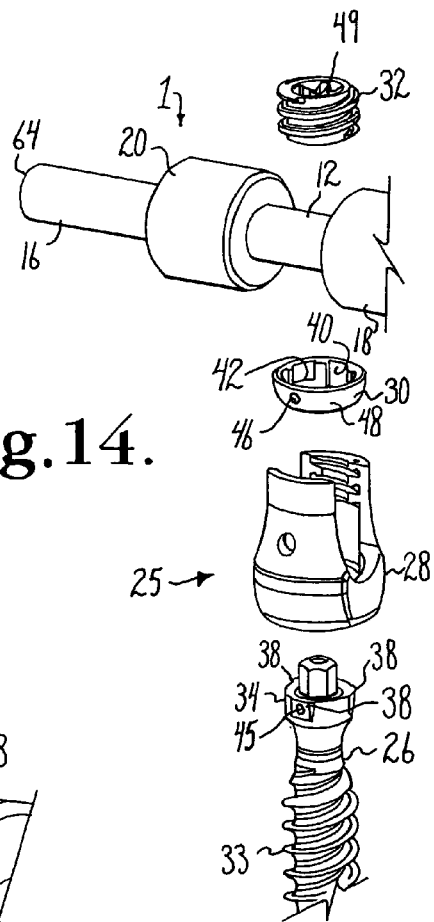
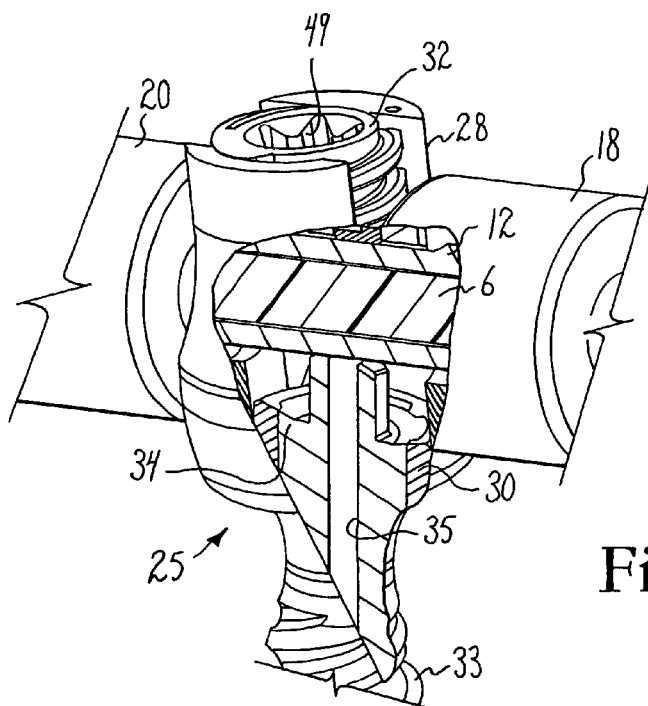
Fig.13.
Fig.14.
Fig.15.

DYNAMIC STABILIZATION CONNECTING MEMBER WITH FLOATING CORE, COMPRESSION SPACER AND OVER-MOLD

CROSS-REFERENCE TO RELATED APPLICATIONS

This application claims the benefit of U.S. Provisional Patent Application Ser. No. 61/201,806, filed Dec. 15, 2008, which is incorporated by reference herein. This application is also a continuation-in-part of U.S. patent application Ser. No. 12/459,492 filed Jul. 1, 2009 that claims the benefit of U.S. Provisional Patent Application Ser. No. 61/134,480, filed Jul. 10, 2008 and claims the benefit of U.S. Provisional Patent Application Ser. No. 61/137,743, filed Aug. 1, 2008, all three of which are incorporated by reference herein. This application is also a continuation-in-part of U.S. patent application Ser. No. 12/287,035 filed Oct. 3, 2008 that claims the benefit of U.S. Provisional Patent Application No. 60/999,965 filed Oct. 23, 2007, both of which are incorporated by reference herein. This application is also a continuation-in-part of U.S. patent application Ser. No. 12/156,260, filed May 30, 2008, that claims the benefit of U.S. Provisional Patent Application Ser. No. 60/932,567, filed May 31, 2007, and the benefit of U.S. Provisional Patent Application Ser. No. 60/994,068, filed Sep. 17, 2007, all three of which are incorporated by reference herein. This application is also a continuation-in-part of U.S. patent application Ser. No. 12/148,465, filed Apr. 18, 2008, that claims the benefit of U.S. Provisional Patent Application Ser. No. 60/927,111, filed May 1, 2007, both of which are incorporated by reference herein.

BACKGROUND OF THE INVENTION

The present invention is directed to dynamic fixation assemblies for use in bone surgery, particularly spinal surgery, and in particular to longitudinal connecting members and cooperating bone anchors or fasteners for such assemblies, the connecting members being attached to at least two bone anchors.

Historically, it has been common to fuse adjacent vertebrae that are placed in fixed relation by the installation therealong of bone screws or other bone anchors and cooperating longitudinal connecting members or other elongate members. Fusion results in the permanent immobilization of one or more of the intervertebral joints. Because the anchoring of bone screws, hooks and other types of anchors directly to a vertebra can result in significant forces being placed on the vertebra, and such forces may ultimately result in the loosening of the bone screw or other anchor from the vertebra, fusion allows for the growth and development of a bone counterpart to the longitudinal connecting member that can maintain the spine in the desired position even if the implants ultimately fail or are removed. Because fusion has been a desired component of spinal stabilization procedures, longitudinal connecting members have been designed that are of a material, size and shape to largely resist bending (including flexion and extension), torsion, distraction and compression, and thus substantially immobilize the portion of the spine that is to be fused. Thus, longitudinal connecting members are typically uniform along an entire length thereof, and usually made from a single or integral piece of material having a uniform diameter or width of a size to provide substantially rigid, inelastic support in all planes.

An alternative to fusion and the use of hard, rigid longitudinal connecting members or other stiff inelastic structures which immobilize at least a portion of the spine, has been a "soft" or "dynamic" stabilization approach in which a bendable and often resilient loop-, S-, C- or U-shaped member or a coil-like and/or a spring-like member is utilized as an elastic longitudinal connecting member fixed between a pair of pedicle screws in an attempt to create, as much as possible, a normal loading pattern between the vertebrae in flexion, extension, distraction, compression, side bending and torsion. Another type of soft or dynamic system known in the art includes bone anchors connected by cords or strands, typically made from a plastic material. Such a cord or strand may be threaded through cannulated spacers that are disposed between adjacent bone anchors when such a cord or strand is implanted, tensioned and attached directly to the bone anchors. The spacers typically span the distance between bone anchors and cooperate with the tensioned cord to provide limited protected movement, thereby strengthening and supporting a region of the spine. Such cord or strand-type systems require specialized bone anchors and tooling for tensioning and holding the cord or strand in the bone anchors. Although bendable, the cords or strands and spacers utilized in such systems do not allow for any significant elastic compression and distraction or elongation of the system in a caudad and/or cephalad direction once implanted because the spacer must be significantly precompressed and the cord or strand must be substantially stretched or pulled to maximum tension in order to provide a stable, supportive system. Such tensioned cord and precompressed spacer systems may also cause undesirable facet joint compression loading during certain spinal movements, especially side bending and flexion, due primarily to this lack of posterior spinal column elongation which significantly alters the normal biomechanics of segmental spinal motion.

The complex dynamic conditions associated with spinal movement create challenges for the design of elongate compressible and/or distractable longitudinal connecting members that exhibit an adequate fatigue strength to provide internal fixation and stabilization for protected motion of the spine, without fusion, and that allow for some natural movement or at least some modified protected motion of the portion of the spine being reinforced and supported by such an elongate connecting member that can be partially or fully elastic. A further challenge are situations in which a portion or length of the spine requires a more rigid stabilization, possibly including fusion, while another portion or length may be better supported by a less stiff and more dynamic system that allows for modified protected spinal motion, again, without fusion.

SUMMARY OF THE INVENTION

A longitudinal connecting member assembly according to the invention has an inner elongate floating core that extends between first and second inelastic rigid bone anchor engaging members, the floating core being partially surrounded by the inelastic members and in slidable relationship therewith. At least one elastic compression spacer or bumper surrounds the core and is slidable along the core, the spacer abutting at least one of the inelastic members. An elastic over-molded member surrounds each spacer and at least a portion of an adjacent inelastic member or members, the over-mold connecting each of the inelastic members with the spacer and elastically resisting distraction. The inner core, elastic spacer and adjacent over-mold cooperate dynamically, with the spacer being compressible and the over-mold being stretchable as well as compressible. In certain embodiments, the over-mold is a hybrid or composite material, for example, having elongate reinforcement strands imbedded in a polymer. The strands may be in sinusoidal form when the over-mold is in a neutral state and in a more linear, elongated form when the over-mold is stretched or distracted, providing strength and toughness during spinal movement. Also in certain embodiments, the free floating core is made from a polymer, such as polyetheretherketone (PEEK), providing for controlled bending as well as shear resistance, although other suitable materials can be used, such as metals including cobalt chrome. Varying the materials can alter or adjust the stiffness of the connecting member.

OBJECTS AND ADVANTAGES OF THE INVENTION

An object of certain embodiments of the invention is to provide dynamic medical implant stabilization assemblies having longitudinal connecting members that include a discrete inner core that can allow for controlled bending and provide shear resistance. Another object of certain embodiments of the invention is to provide such an inner core that does not limit compression or distraction of elastic members of the implant. Another object of certain embodiments of the invention is to provide such an assembly including an elastic spacer and elastic over-mold combination, the spacer operating in compression, the over-mold primarily in tension. A further object of the invention is to provide dynamic medical implant longitudinal connecting members that may be utilized with a variety of monoaxial and polyaxial bone screws, hooks and other bone anchors. Additionally, it is an object of the invention to provide a lightweight, reduced volume, low profile assembly including at least two bone anchors and a longitudinal connecting member therebetween. Furthermore, it is an object of the invention to provide apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 13 is an enlarged perspective view of the second anchor engaging member of FIG. 4 with portions broken away to show the detail thereof.

FIG. 14 is an enlarged and partial perspective view of the connecting member of FIG. 1 shown with one of the bone screws in exploded and partial perspective view.

FIG. 15 is an enlarged and partial perspective view of the assembly of FIG. 1, shown with one bone screw with portions broken away to show the detail thereof.

DETAILED DESCRIPTION OF THE INVENTION

Figure 1:
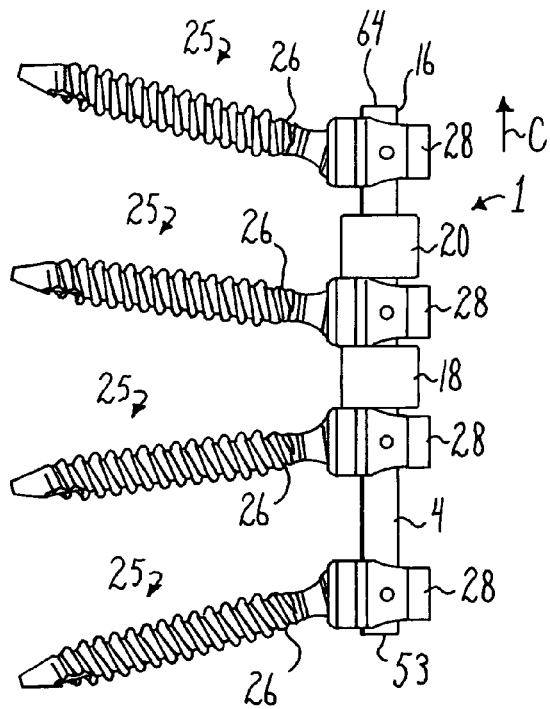
FIG. 1 is a side elevational view of a dynamic fixation connecting member assembly according to the invention shown with four bone screws and in an operative position with respect to a human spine (not shown).
Figure 2:
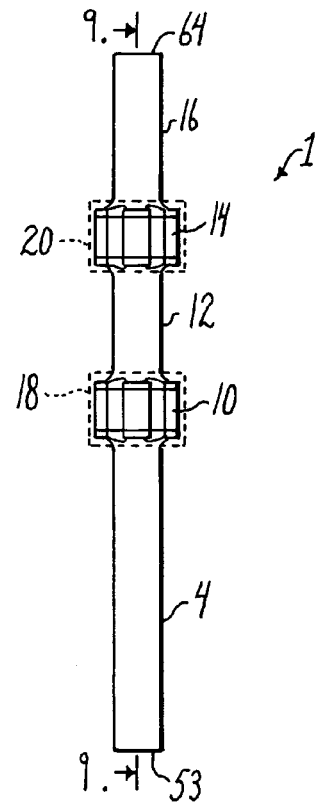
FIG. 2 is an enlarged side elevational view, similar to FIG. 1 shown without the bone screws and with over-molded portions shown in phantom.
Figure 3:
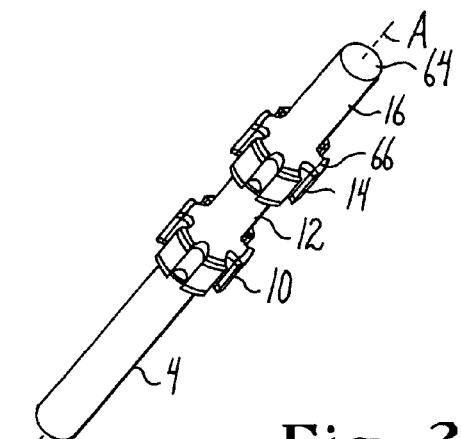
FIG. 3 is a perspective view of the assembly of FIG. 2 shown without over-molds.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the connecting member assemblies of the application and cooperating bone anchors in actual use.

With reference to FIGS. 1-21, the reference numeral 1 generally designates a non-fusion dynamic stabilization longitudinal connecting member assembly according to the present invention. The connecting member assembly 1 includes a first anchor member 4, an elongate inner floating core 6; a first compression spacer 10; a slidable sleeve or trolley tube 12; a second compression spacer 14; and a second anchor member 16; all substantially axially aligned with respect to a central axis A of the assembly 1. The elongate core 6 is receivable within a portion of the first and second anchors 4 and 16 and extends entirely through the spacers 10 and 14 and the sleeve or trolley tube 12. An over-mold or elastic outer sleeve 18 surrounds a portion of the anchor member 4, the first spacer 10 and a portion of the sleeve or trolley tube 12. A second over-mold or elastic outer sleeve 20 surrounds an opposite portion of the trolley tube 12, the second spacer 14 and a portion of the anchor 16. The over-mold 18 attaches the anchor 4 to the spacer 10 and the trolley tube 12 and the over-mold 20 attaches the anchor 16 to the spacer 14 and the sleeve or trolley tube 12. The over-molds 18 and 20 also stretch when the assembly 1 is distracted or tensioned. Both the over-molds 18 and 20 and the spacers 10 and 14 are compressible. It is noted that the spacers 10 and 14 may be of different durometers or geometries to allow for greater or lesser movement of the trolley tube 12 in a desired direction. The spacers engage flared-out flanged ends of the trolley tube that extend exterior to the screw head. For example, when fully assembled and all components fixed in position, as shown in FIG. 1, for example, along a human spine with the anchor 15 being at an upper or cephalad position, varying elasticities of the spacers 10 and 12 may allow for more movement of a portion of the assembly 1 in a cephalad or cranial direction (indicated by the arrow C) and more limited movement in a caudad direction.

As illustrated in FIG. 1, the dynamic connecting member assembly 1 cooperates with at least three bone anchors and is illustrated with four bone anchors in the form of polyaxial bone screws, generally 25, the assembly 1 being captured and fixed in place at the anchor portion 4, the trolley tube 12 and the anchor portion 16 by the bone screws 25. Because the anchor portions 4 and 16 and the trolley tube 12 have substantially hard, inelastic cylindrical surfaces, the connecting member assembly 1 may be used with a wide variety of bone screws and other bone anchors already available for cooperation with more rigid rods including fixed, monoaxial bone screws, hinged bone screws, polyaxial bone screws, and bone hooks and the like, without or with compression inserts within the polyaxial head of the bone anchors, that may in turn cooperate with a variety of closure structures having threads, flanges, or other structure for fixing the closure structure to the bone anchor, and may include other features, for example, external or internal drives, break-off tops and inner set screws. The bone anchors, closure structures and the connecting member assembly 1 are then operably incorporated in an overall spinal implant system for correcting degenerative conditions, deformities, injuries, or defects to the spinal column of a patient. In certain embodiments of the invention wherein the trolley tube 12 is relatively thin, the bone screws may be desirably equipped with upper and/or lower inserts that closely cradle the trolley tube 12 and prevent the trolley tube 12 from pressing against the core 6 and prohibiting relative sliding movement of the floating core 6 with respect to the anchor engaging members 4 and 16.

Generally, each illustrated screw 25, as best shown in FIGS. 14 and 15, includes a shank 26, a receiver or head 28, a retainer structure or ring 30 and a closure structure 32. The shank 26 further includes a threaded portion 33 for driving into a vertebra (not shown) and an upper portion 34 for attachment to the retainer structure 30 and for engagement with the assembly 1. The illustrated shank 26 that is fixedly attached to the retainer ring 30 is pivotally connected to the open receiver or head 28 by sliding cooperation between the retainer ring 30 and the receiver 28. The shank 26 further includes an optional central cannula or through-bore 35 disposed along an axis of rotation of the shank 26. The through bore 35 provides a passage through the shank interior for a length of wire or pin inserted into the vertebra prior to the insertion of the shank 26, the wire or pin providing a guide for insertion of the shank 26 into the vertebra. The receiver 28 includes a pair of spaced and generally parallel arms that form an open generally U-shaped channel therebetween that is open at distal ends of such arms. The receiver arms each include radially inward or interior surfaces that have a discontinuous guide and advancement structure mateable with cooperating structure on the closure structure 32. The guide and advancement structure may be a partial helically wound flange form configured to mate under rotation with a similar structure on the closure structure 32 or a buttress thread, a square thread, a reverse angle thread or other thread like or non-thread like helically wound advancement structure for operably guiding under rotation and advancing the closure structure 32 downward between the receiver arms and having such a nature as to resist splaying of the receiver arms when the closure structure 32 is advanced there-between.

At the factory, the illustrated shank 26 is bottom loaded into the receiver 28 and the retainer ring 30 is top loaded into the receiver 28. The shank upper portion 34 is aligned with respect to the retainer ring 30 such that projections 38 of the upper portion 34 are passed through recesses 40 of the ring 30. The shank 26 is then rotated with respect to the ring 30 until the projections 38 are located directly above projections or shelves 42 located on the ring 30 between each of the recesses 40. The shank 26 is then moved downwardly and the shank projections 38 engage the shelves 42 of the retainer ring 30. A tool (not shown) is then used to crimp the retainer ring 30 into frictional engagement with the shank 26 at aligned locations 45 of the shank upper portion 34 and 46 of the retainer ring 30. The retainer ring 30 includes an outer curved surface 48 for sliding, pivotal engagement with an inner surface of the receiver 28. Specifically, the illustrated retaining structure 30 curved surface 48 is a partially spherical surface that is slidingly mateable with a cooperating partially spherical inner surface of the receiver 28, allowing for a wide range of pivotal movement between the shank 26 and the receiver 28.

It is noted that a variety of polyaxial connections are possible for the bone screws or other anchors that cooperate with longitudinal connecting member assemblies of the invention. For example, a spline capture connection as described in U.S. Pat. No. 6,716,214, and incorporated by reference herein, may also be used wherein the bone screw shank also includes an upper portion mateable with a retaining structure disposed within the receiver. Polyaxial bone screws with other types of capture connections may also be used according to the invention, including but not limited to, threaded connections, frictional connections utilizing frusto-conical or polyhedral capture structures, integral top or downloadable shanks, and the like. Also, as indicated above, polyaxial and other bone screws for use with connecting members of the invention may have bone screw shanks that attach directly to the connecting member or may include compression members or inserts that engage the bone screw shank and cooperate with the shank, the receiver and the closure structure to secure the connecting member assembly to the bone screw and/or fix the bone screw shank at a desired angle with respect to the bone screw receiver that holds the longitudinal connecting member assembly. Furthermore, although the closure structure 32 of the present invention is illustrated with the polyaxial bone screw 25 having an open receiver or head 28, it is foreseen that a variety of closure structures may be used in conjunction with any type of medical implant having an open or closed head or receiver, including monoaxial bone screws, hinged bone screws, hooks and the like used in spinal surgery.

To provide a biologically active interface with the bone, the threaded portion 33 of the shank 26 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding. It is also foreseen that combinations of the above can be used, such as a composite of titanium plasma spray and hydroxyapatite.

The closure structure 32 can be any of a variety of different types of closure structures for use in conjunction with the present invention with suitable mating structure on the interior surface of the upstanding arms of the receiver 28. The illustrated closure structure 32 is rotatable between the spaced arms of the receiver 28. However, two piece closures or other types of single piece closures, such as slide-in closure structures and 90° twist-in closures may be used as an alternative to helically wound closures. The illustrated closure 32 is substantially cylindrical and includes an outer helically wound guide and advancement structure in the form of a flange form that may take a variety of forms, including those described in Applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure downward between the receiver arms and having such a nature as to resist splaying of the arms when the closure structure is advanced into the U-shaped channel formed by the arms. The illustrated closure structure 32 includes an internal drive feature 49 for rotating and driving the closure 32 into the receiver 28. It is foreseen that the closure structure may alternatively include an external drive, such as a break-off head designed to allow such a head to break from a base of the closure at a preselected torque, for example, 60 to 120 inch pounds. Such a closure structure would also include a base having an internal drive to be used for closure removal.

Figure 4:
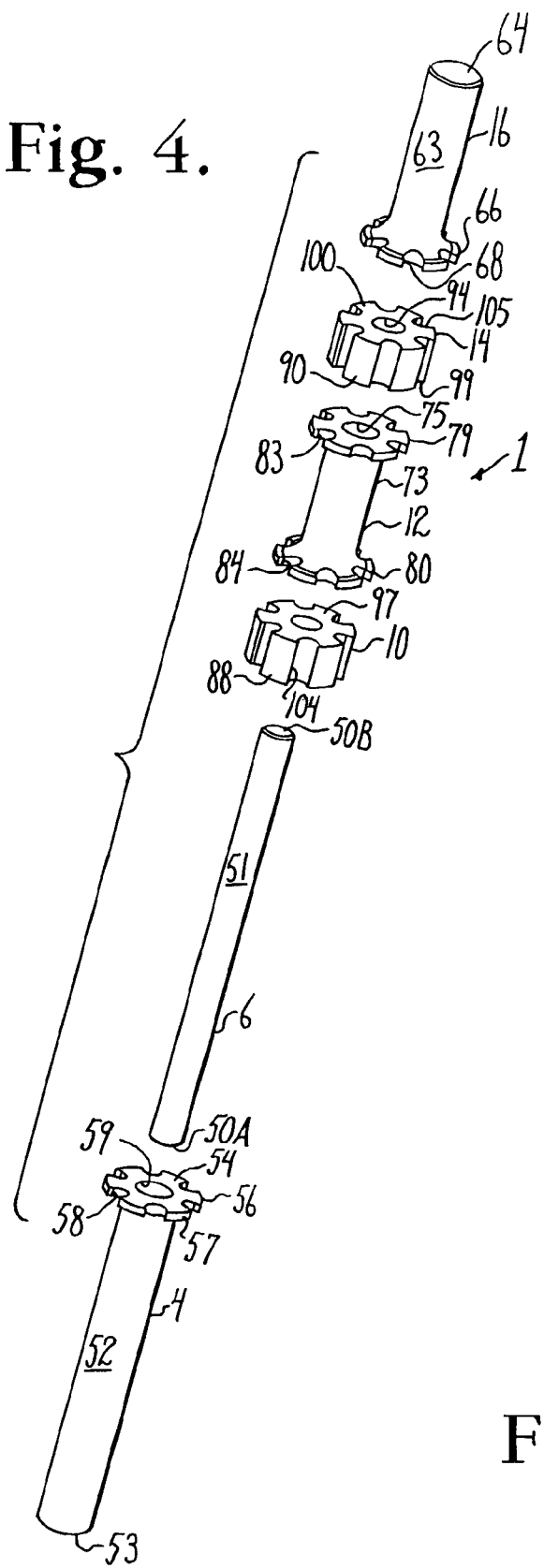
FIG. 4 is an enlarged exploded perspective view of the assembly of FIG. 3 including a first end, anchor engaging member, a floating core, a first spacer, a sleeve anchor engaging member, a second spacer and a second end anchor engaging member.
Figure 9:
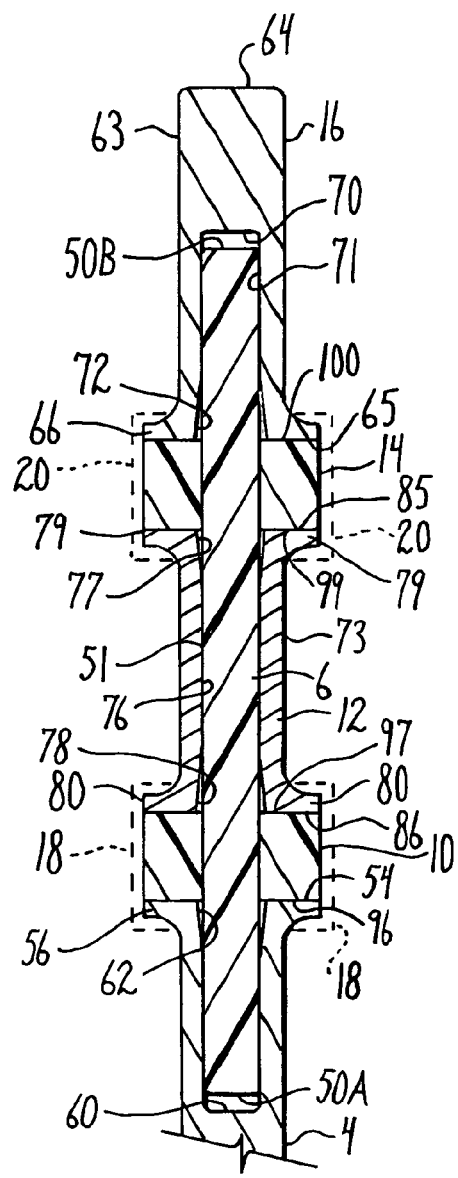
FIG. 9 is an enlarged and partial cross-sectional view taken along the line 9-9 of FIG. 2.
Figure 10:
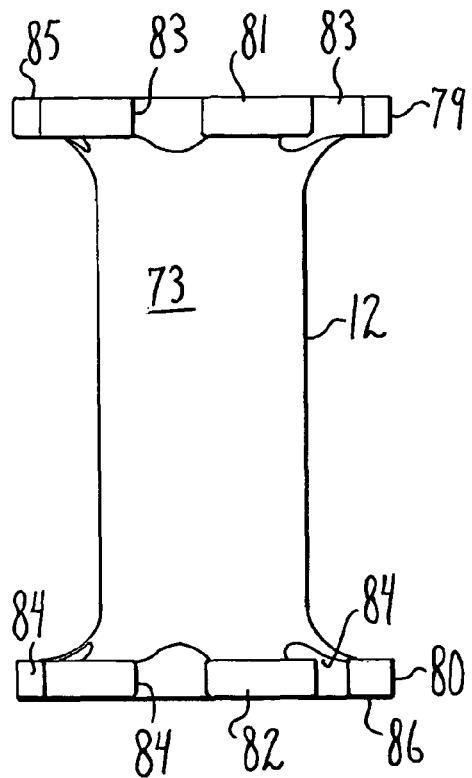
FIG. 10 is an enlarged side elevational view of the sleeve member of FIG. 4.
Figure 11:
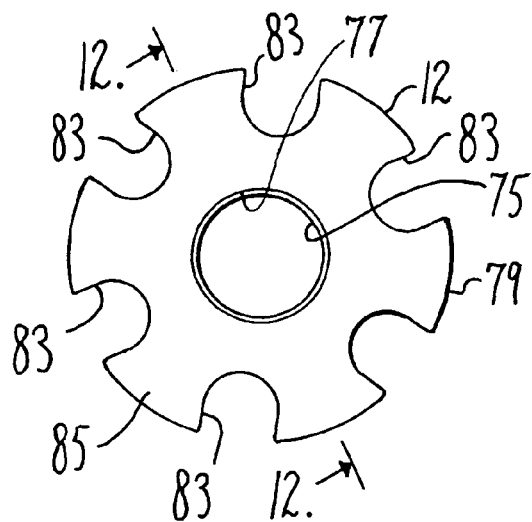
FIG. 11 is an enlarged top plan view of the sleeve of FIG. 4.
Figure 12:
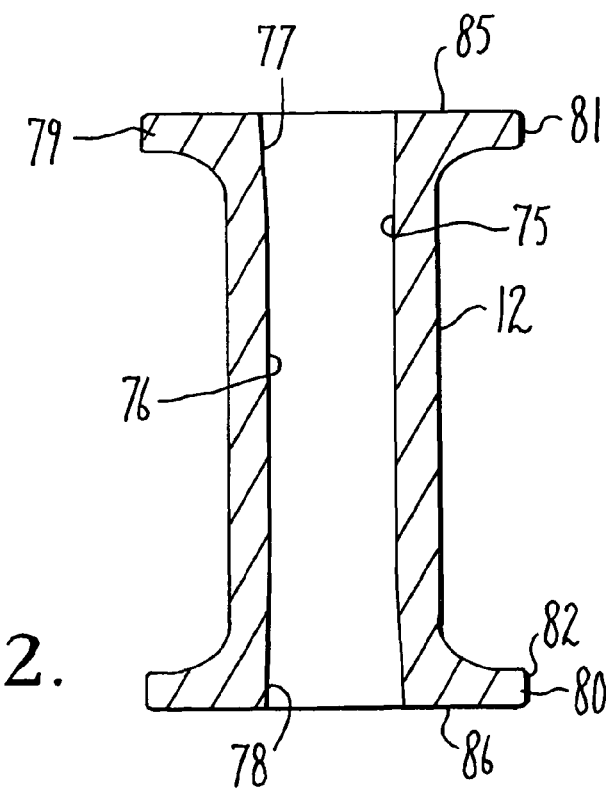
FIG. 12 is a cross-sectional view taken along the line 12-12 of FIG. 11.

Returning to the longitudinal connecting member assembly 1, the inner core 6, best illustrated in FIGS. 4 and 9 is elongate, substantially solid, smooth and in the form of a uniform cylinder or rod having an outer cylindrical surface 51 substantially circular in cross-section. As will be described in greater detail below, the core 6 is sized and shaped to slidingly fit within apertures or partial bores of the anchor members 4 and 16. The core 6 is slightly shorter in length than a distance along the axis A that spans between ends of the bores of the anchor members 4 and 16 such that the core 6 may freely slide or "float" within a void formed by and between the anchor members 4 and 16, the spacers 10 and 14 and the trolley tube 12, the core 6 assisting protective bending and providing shear resistance for the assembly 1 when such forces are applied. The core 6 and the anchor engaging members 4 and 16 may be made from metal, metal alloys, such as cobalt chrome, or other suitable materials, including plastic polymers, such as polyetheretherketone (PEEK), ultra-high-molecular weight-polyethylene (UHMWP), polyurethanes and composites, including composites containing carbon fiber and layers of different materials. A PEEK core 6 is preferred. The core can be made of pure PEEK as well as carbon fiber reinforced PEEK. It is noted that the core 6 and anchor members 4 and 16 may be made from the same or different materials, with metals and metal alloys being preferred for the anchor members 4 and 16.

Figure 5:
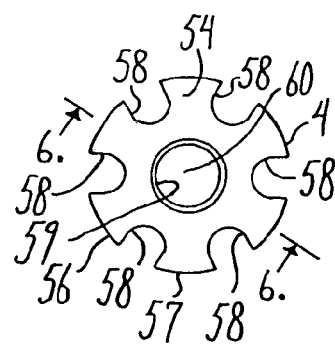
FIG. 5 is an enlarged top plan view of the first anchor engaging member of FIG. 4.
Figure 6:
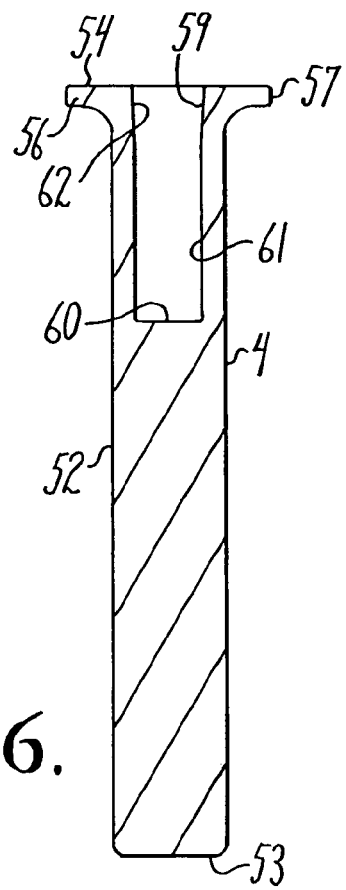
FIG. 6 is an enlarged cross-sectional view taken along the line 6-6 of FIG. 5.
Figure 7:
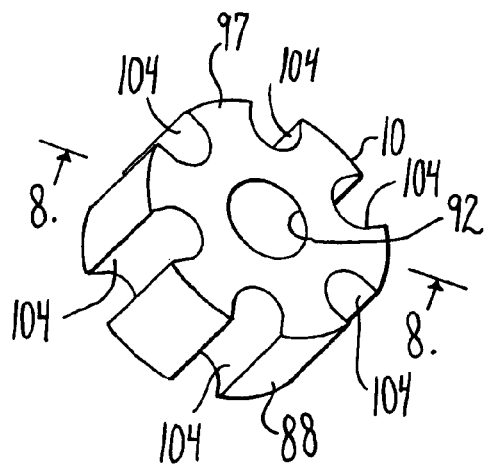
FIG. 7 is an enlarged perspective view of the first spacer of FIG. 4.
Figure 8:
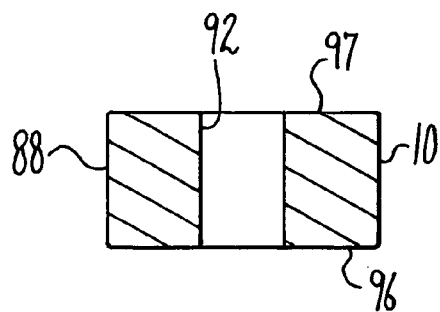
FIG. 8 is a cross-sectional view taken along the line 8-8 of FIG. 7.

With particular reference to FIGS. 4-6, 9 and 13, the inelastic anchor members 4 and 16 are substantially identical with the exception that the member 16 is shorter in length along the axis A than the member 4. As illustrated, the member 4 is sized to receive two bone screws 25 while the member 16 is sized to receive one bone screw 25. The members 4 and 16 may be designed to be longer or shorter as needed for the particular use and/or may be cut at the end opposite thereof to a flared-out flanged end or buttress plate thereof to a specific length required by the surgeon so as to receive one or more bone screws 25 or other types of bone anchors. Both members 4 and 16 are cylindrical along an entire length thereof along the axis A and include at least two or more circular cross-sections along the length thereof. With particular reference to FIGS. 4-6, the member 4 includes a substantially cylindrical surface 52, an end 53 and an opposed end 54 that partially defines an end or buttress plate 56. In use, the buttress plate or flared-out flanged end extends exterior to the screw head. The buttress plate 56 has a cylindrical surface 57 with at least one and up to a plurality of grooves 58 for gripping the over-mold 18. The illustrated buttress plate 56 includes six equally spaced U-shaped grooves 58, each groove formed in the surface 57 and extending toward the axis A. Each groove 58 also extends through the plate 56 in a direction substantially parallel to the axis A. Formed in the end surface 54 of the member 4 is a partial bore or aperture 59 sized and shaped to closely slidingly receive the floating core 6. As best illustrated in FIG. 6, the partial bore 59 does not extend through the anchor to the end 53. The partial bore 59 is substantially defined by a substantially planar end surface 60, a cylindrical surface 61 and a flared, radiused, or frusto-conical surface 62 disposed between the cylindrical surface 61 and opening and widening at the end surface 54.

With particular reference to FIGS. 4, 9 and 13, the member 16 includes a substantially cylindrical surface 63, an end 64 and an opposed end 65 that partially defines a buttress plate 66. The buttress plate 66 has a cylindrical surface 67 with at least one and up to a plurality of grooves 68. The illustrated buttress plate 66 includes six equally spaced U-shaped grooves 68, each groove formed in the surface 67 and extending toward the axis A. Each groove 68 also extends through the plate 66 in a direction substantially parallel to the axis A. Formed in the end surface 65 of the member 16 is a partial bore or aperture 69 sized and shaped to closely slidingly receive the floating core 6. The partial bore 69 is substantially defined by a substantially planar end surface 70 that is spaced from the end 64, the anchor 16 being substantially solid between the end surface 70 and the end 64. The bore 69 is further defined by a cylindrical surface 71 and a flared, radiused, or frusto-conical surface 72 disposed between the cylindrical surface 71 and the end surface 65, the surface 72 widening running in a direction toward the end surface 65. Although the illustrated anchor members 4 and 16 and the core 6 are substantially cylindrical, it is foreseen that the components 4, 16 and 6 may have other forms, including but not limited to oval, square and rectangular cross-sections as well as other curved or polygonal shapes.

With particular reference to FIGS. 9-12, the trolley tube 12 is sized and shaped to be slidingly received over the core 6 along the axis A and have a length measured along the axis A that is sufficient for the attachment of at least one bone screw 25 thereon. Although only one trolley tube 12 is illustrated in the assembly 1, it is noted that other, longer assemblies according to the invention may include additional sleeves or trolley tubes 12 for attachment with additional bone screws along a length of a spine. Such embodiments also require additional spacers similar to the spacer 10 positioned between trolley tubes and adjacent to each bone anchor 4 and 16. Furthermore, shorter embodiments according to the invention may omit the trolley tube 12, such as the assembly 201 described below, which can include only 2 bone anchors.

Similar to the anchor members 4 and 16, the sleeve or trolley tube 12 may be made from a substantially inelastic material, such as metal, metal alloys or other suitable materials, including plastic polymers such as polyetheretherketone (PEEK), ultra-high-molecular weight-polyethylene (UHMWP), polyurethanes and composites, including composites containing carbon fiber. The trolley tube 12 may be made of the same or different material than the cooperating floating core 6. In order to have low or no wear debris, the trolley tube 12 inner surface and also the surfaces defining the inner bore 59 of the anchor 4 and the surfaces defining the inner bore 69 of the anchor 16 may be coated with an ultra thin, ultra hard, ultra slick and ultra smooth coating, such as may be obtained from ion bonding techniques and/or other gas or chemical treatments. The trolley tube and core can also be made from cobalt chrome which provides for good wear characteristics.

The illustrated trolley tube 12 is substantially cylindrical, having an outer cylindrical bone anchor attachment surface 73 that is of substantially the same diameter as the outer surface 52 of the anchor member 4 and the outer surface 63 of the anchor member 16. The trolley tube 12 further includes a through bore 75 defined by a substantially cylindrical inner surface 76 and an opposed pair of flared, radiused, or frusto-conical surfaces 77 and 78. The inner surfaces 76, 77 and 78 form a curved, slightly hour-glass configuration running along the axis A that decreases both bending stresses along the core 6 and wear debris between the core 6 and the trolley tube 12. For example, if the core 6 is flexed, the inner surfaces 77 and 78 allow deformation of the core over a longer area or length resulting in reduced stresses and a longer fatigue life. Furthermore, if the core 6 is made from a material such as PEEK, the curved or flared surfaces 77 and 78 reduce contact wear and bending stresses along the core 6 surface that is received in the trolley tube 12. The flared surface 62 of the anchor member 4 and the flared surface 72 of the anchor member 16 also function in such a fatigue and wear reducing manner. The trolley tube 12 includes a pair of opposed end plates 79 and 80. The illustrated plates 79 and 80 have outer cylindrical surfaces 81 and 82, respectively, that have respective grooves 83 and 84 formed therein. The grooves 83 and 84 are identical or substantially similar to the grooves 58 of the anchor 4 and the grooves 68 of the anchor 16 previously described herein. As will be described in greater detail below, when assembled, the grooves 58 align with grooves of the spacer 10 and also with the grooves 84, providing a channel for the flow and eventual set up and gripping of the polymer of the over-mold 18 and the grooves 68 align with grooves of the spacer 14 and also with the grooves 83, providing a flow receiving and gripping channel for the polymer material of the over-mold 20. The plates 79 and 80 are of substantially the same outer diameter as the buttress plate outer cylindrical surfaces 57 and 67 of respective anchor members 4 and 16. The trolley tube 12 includes opposed planar end surfaces 85 and 86. However, the surfaces 85 and 86 may be curved (convex or concave) as will be described with respect to other embodiments of the invention.

With particular reference to FIGS. 4 and 7-9, the elastic spacers 10 and 14 are sized and shaped to be slidingly received over the core 6 and may be made from a variety of elastic materials of the same or different durometers and materials, including, but not limited to natural or synthetic elastomers such as polyisoprene (natural rubber), and synthetic polymers, copolymers, and thermoplastic elastomers, for example, polyurethane elastomers such as polycarbonate-urethane elastomers. In order to have low or no wear debris, the spacers 10 and 14 inner and side surfaces may also be coated with an ultra thin, ultra hard, ultra slick and ultra smooth coating, such as may be obtained from ion bonding techniques and/or other gas or chemical treatments.

The illustrated spacers 10 and 14 advantageously cooperate with the core 6, the trolley tube 12 and the anchor members 4 and 16, providing directed axial movement, limitation and protection of movement by the trolley tube 12 along the core 6 located between bone screws 25. The illustrated spacers 10 and 14 are identical or substantially similar in size and geometry. Each of the spacers 10 and 14 have an external substantially cylindrical outer surface 88 and 90, respectively, and internal surfaces 92 and 94, respectively, each defining through bores of substantially circular cross-section. The internal surfaces may further be defined by a curved or hour glass surface in some embodiments of the invention. The spacer 10 includes opposed substantially planar and annular end surfaces 96 and 97 and the spacer 14 includes opposed substantially planar and annular end surfaces 99 and 100. When cooperating with the core 6, the end surfaces 96 and 97 and 99 and 100 are substantially perpendicular to the axis A. It is foreseen that in some embodiments, the spacers 10 and 14 may be of square, rectangular or other cross-section, including curved or polygonal shapes with matching configurations for the buttress plates. The size of the internal surfaces 92 and 94 allow for some axially directed sliding movement of the respective spacers 10 and 14 with respect to the core surface 51. In the illustrated embodiment, both the spacers 10 and 14 further include respective grooves 104 and 105 formed in respective cylindrical surfaces 88 and 90, the grooves 104 and 105 being sized, oriented and spaced similar to the grooves 58, 68, 83 and 84 previously described herein with respect to the anchor members 4 and 16 and the trolley tube 12. The grooves 104 align and cooperate with the grooves 58 and 84 during molding of the elastic over-mold 18 while the grooves 105 align and cooperate with the grooves 83 and the grooves 68 during molding of the elastic over-mold 20.

Figure 21:
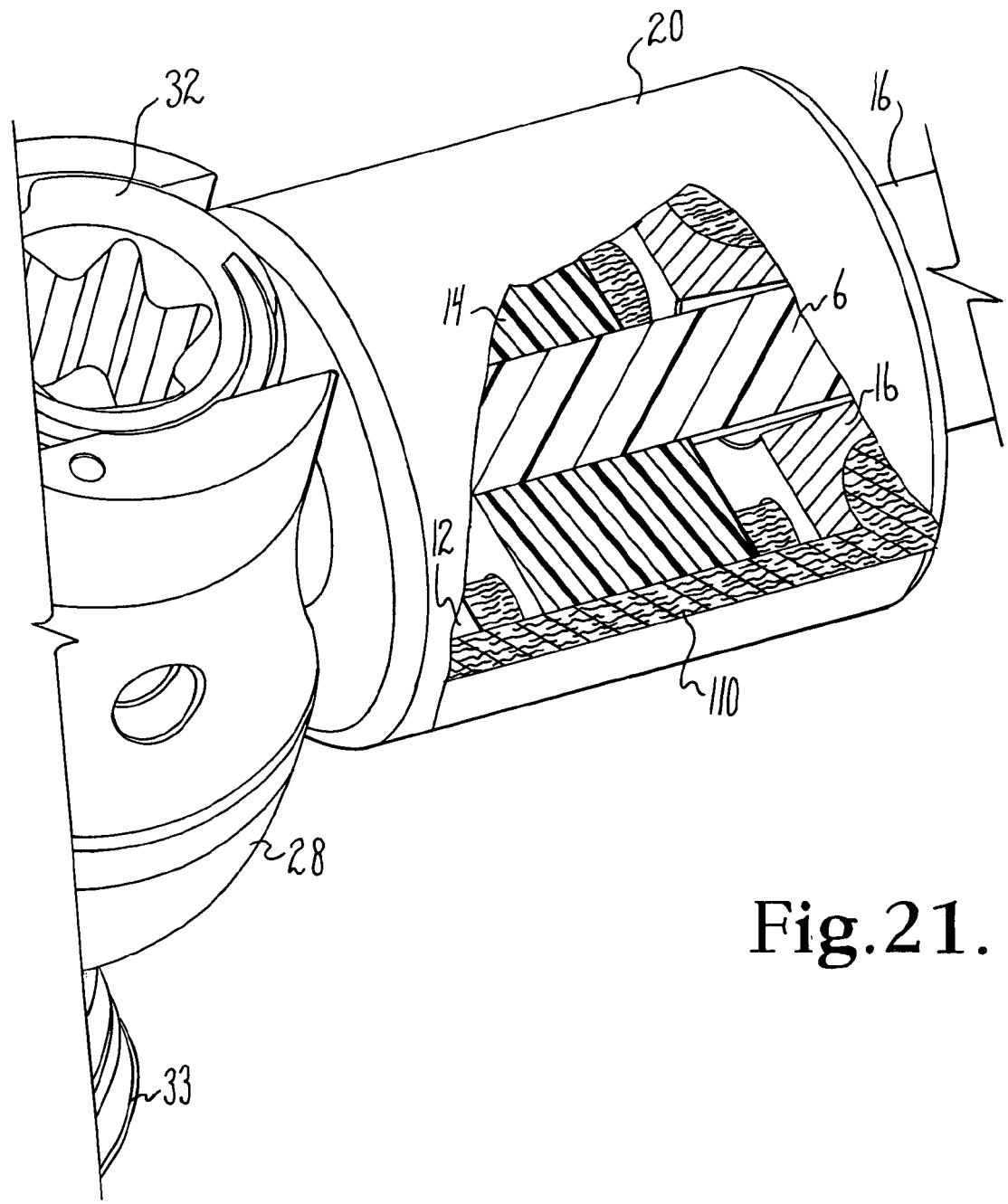
FIG. 21 is an enlarged and partial perspective view, similar to FIG. 20, showing the assembly of FIG. 1 in an expanded, stretched state of FIG. 17.

With particular reference to FIGS. 1, 2, 9, 20 and 21, the elastic over-molded coverings 18 and 20 have a number of functions, including, but not limited to: 1) to hold the component anchors, spacers and sleeve of the assembly 1 adjacent one another and in close or touching relationship when in a neutral state; 2) to allow for elastic distraction of the assembly 1, the component anchors, spacer and sleeve being separated or spaced from one another during distraction of the assembly 1 and yet being securely held near one another by the over-molds 18 or 20; 3) to compress and allow for compression of the spacers when the assembly 1 is placed in compression by spinal movement; 4) to readily bend in any direction in response to spinal movement and to readily allow, yet resist, torsion or twisting; and 5) to provide protection to the body by keeping wear debris within the assembly 1 and keeping scar tissue out of the assembly 1 at junctures between the anchors spacers and sleeve. For example, when the assembly 1 is placed in tension as shown in FIG. 21, the over-molds 18 and 20 advantageously expand while gripping to a sleeve, spacer and anchor as well as provide a covering over the components that may separate, for example, the illustrated spacer 14 and the anchor 16, guarding against gaps that might otherwise irritate scar and surrounding body tissue that could get trapped or pinched in between. It is foreseen in some embodiments that the over-molds could be eliminated.

The over-molded portions or sections 18 and 20 may be made of a variety of materials including natural and synthetic plastics and composites. The illustrated over-molds 18 and 20 are a molded thermoplastic elastomer, for example, polyurethane or a polyurethane blend; however, any suitable polymer material may be used. Furthermore, in order to provide strength to the over molds 18 and 20 and guard against tearing or other breakage, the illustrated over-molds 18 and 20 are hybrid/composites, that include curved or sinusoidal strands 110 of a resilient and/or bendable material present in the molded thermoplastic elastomer, such as, for example, polyester strands that are curled or coiled when the over-mold is in a neutral state, as shown by the over-mold 20 in FIG. 20 and straighten when the over-mold is tensioned and stretched, such as shown by the over-mold 20 with strands 110 in FIG. 21. The strands 110 located in the polymer disposed in the aligned grooves of the anchors, spacers and sleeve provide reinforcement for the over-molds 18 and 20 in both the neutral and stretched state, and in particular in the stretched or distracted state. Other materials may be used in place of the strands 110 to provide strength during stretching of the over-molds 18 and 20, such as woven or otherwise linked threads, strands, or other reinforcement material.

As best shown in FIG. 9, the illustrated over-mold 18 is fabricated around and about the entire plate 56 of the anchor 4, the entire spacer 10, and the entire end plate 80 of the trolley tube 12. The illustrated over-mold 20 is fabricated around and about the surfaces of the end plate 79 of the trolley tube 12, the entire spacer 14, and the entire end plate 66 of the anchor 16.

The over-molds 18 and 20 are fabricated from an initially flowing elastomer, as will be described more fully below, with the elastomer engaging and possibly adhering to the end plate surfaces of the anchor members 4 and 16 and both end plates of the trolley tube 12 as well as the outer surface of the spacers 10 and 14. Each formed elastomer is substantially cylindrical, but thinner than the spacers 10 and 14 so as to also be bendable and deformable when the assembly 1 is bent, compressed or stretched as shown, for example, in FIGS. 16-19 and 20-21. In both spinal flexion and extension, the over-molds 18 and 20 completely surround or cover the assembly 1 components as also illustrated in the drawing figures. It is foreseen that the material for the over-molds 18 and 20 may be sized and made from such materials so as to provide for relatively more or less bendability, compressibility and stretchability. Curing the over molded polymer in a vacuum is preferred.

The illustrated dynamic connecting member assembly 1 is shown cooperating with four polyaxial bone screws 25 in FIG. 1. In use, the bone screws 25 are implanted into vertebrae (not shown). Each vertebra may be pre-drilled to minimize stressing the bone. Furthermore, when a cannulated bone screw shank is utilized, each vertebra will have a guide wire or pin inserted therein that is shaped for the bone screw cannula of the bone screw shank 26 and provides a guide for the placement and angle of the shank 26 with respect to the cooperating vertebra. A further tap hole may be made and the shank 26 is then driven into the vertebra by rotation of a driving tool (not shown) that engages a driving feature (shown as a hex head) on the upper portion 34 of the bone screw 25. It is foreseen that both the screws 25 and the longitudinal connecting member assembly 1 may be inserted in a conventional, percutaneous or other minimally invasive surgical manner.

With particular reference to FIGS. 1, 4, 9, 14 and 15, the longitudinal connecting member assembly 1 is assembled by inserting the core 6 end 50A into the bore 59 of the anchor member 4. The core 6 readily slides into the bore 59 and is held in place by gripping tools (not shown) while other members of the assembly 1 are loaded onto the core 6. Specifically, the spacer 10 is next loaded onto the core 6 by inserting the spacer 10 onto the end 50B of the core 6 with the internal surface 92 of the spacer 10 being slidable along the core surface 51 until the spacer 10 abuts against the end surface 54 of the buttress plate 56 of the first anchor member 4. The trolley tube 12 is then threaded on the core 6 at the end 50B with the end surface 86 facing the end surface 97 of the spacer 10. The trolley tube 12 is slid along the core 6 until the trolley tube 12 abuts against the spacer 10. It is noted that the illustrated trolley tube 12 may be loaded onto the core 6 at either end surface 85 or 86 thereof, with the surfaces 76, 77 and 78 being slidable along the surface 51. The second spacer 14 is then threaded on the core 6 at the end 50B with the end surface 99 facing the end surface 85 of the trolley tube 12. The spacer 14 is slid along the core surface 51 until the spacer 14 abuts against the trolley tube 12. As with the trolley tube 12, the illustrated spacers 10 and 14 may be loaded onto the core at either end surface thereof. The core 6 is then received in the bore 69 of the second anchor member 16. The anchor member 16 is slid along the core 6 until the surface 65 of the buttress plate 66 abuts against the second compression spacer 14. Manipulation tools (not shown) are used to grasp the anchor member 4 at the surface 52 near the end 53 and the anchor member 16 at the surface 63 near the end 64, pressing the anchor members 4 and 16 toward one another to place the anchor member 4 into contact engagement with the spacer 10, the spacer 10 into contact engagement with the trolley tube 12, the trolley tube 12 into contact engagement with the spacer 14 and the spacer 14 into contact engagement with the anchor member 16. At this time, the grooves 58, 104, 84, 83, 105 and 68 are aligned as shown, for example, in FIG. 3. In some embodiments of the invention, a desired amount of axial compressive force may be placed on the components loaded on the core 6 at this time. The over-mold 18 is then fabricated around and about the buttress plate 56, the spacer 10 and the end plate 80. The over-mold 20 is fabricated around and about the end plate 79, the spacer 14 and the buttress plate 66. In a preferred method of fabrication of the over-molds 18 and 20, an elastic, polymeric material, such as a urethane elastomer with reinforced strands, flows about the desired components of the assembly 1, filling spaces between the grooves 58, 104, 84, 83, 105 and 68 at room temperature, followed by a vacuum cure. In the illustrated embodiment, the over-molds 18 and 20 are fabricated about the assembly 1 components without compressing the spacers 10 and 14. In other embodiments, the over-molds 18 and 20 may be fabricated about the spacers 10 and 14 after an initial compression of the spacers.

After over molds 18 and 20 are cured, the holding tools are removed. The spacers 10 and 14 and the trolley tube 12 are slidable with respect to the core 6, but are limited by the buttress plates of the anchor members 4 and 16 and the end plates of the trolley tube 12. In some embodiments, the spacers 10 and 14 place a distractive force on the over molds 18 and 20. Whether in a neutral or compressed state, the spacers 10 and 14 are able to respond to jolting and other body movements and thereafter spring back into an originally set location after the particular movement is completed. In a preferred embodiment, the spacers 10 and 14 primarily compress in response to axial and bending forces, while the over molds 18 and 20 stretch and compress in response to axial and bending forces.

With reference to FIGS. 1 and 15-19, the assembly 1 is eventually positioned in an open or percutaneous manner in cooperation with the bone screws 25 with the over-molds 18 and 20 disposed between bone screws 25, with at least one bone screw 25 attached to each of the anchor members 4 and 16 and to the trolley tube 12. In the illustrated embodiment, two bone screws 25 are attached to the anchor member 4. A closure structure 32 is used to attach each screw 25 to the assembly 1.

Figure 16:
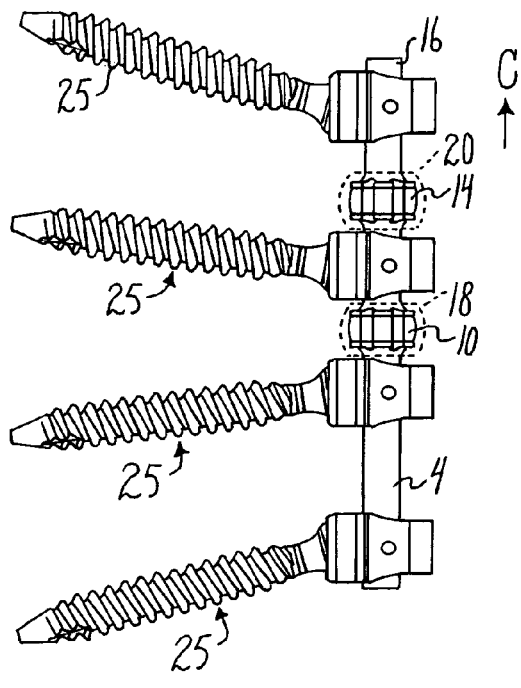
FIG. 16 is a side elevational view of the assembly of FIG. 1 with over-molds shown in phantom and spacers shown in compression.
Figure 17:
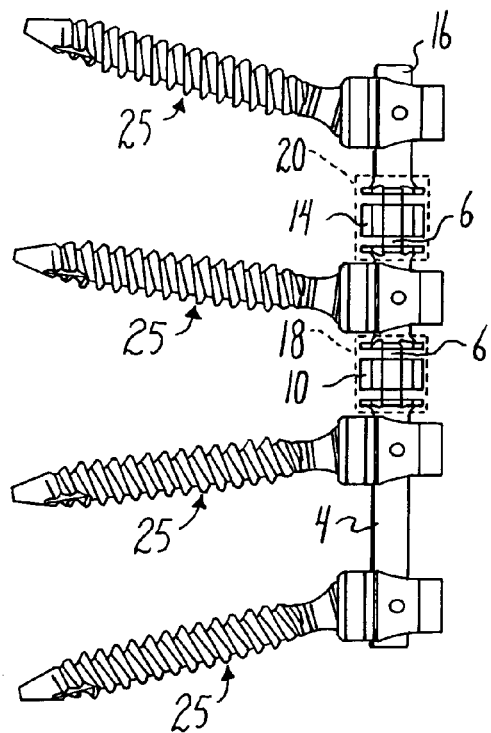
FIG. 17 is a side elevational view of the assembly of FIG. 1 with over-molds shown in phantom and the assembly shown expanding under tension.
Figure 18:
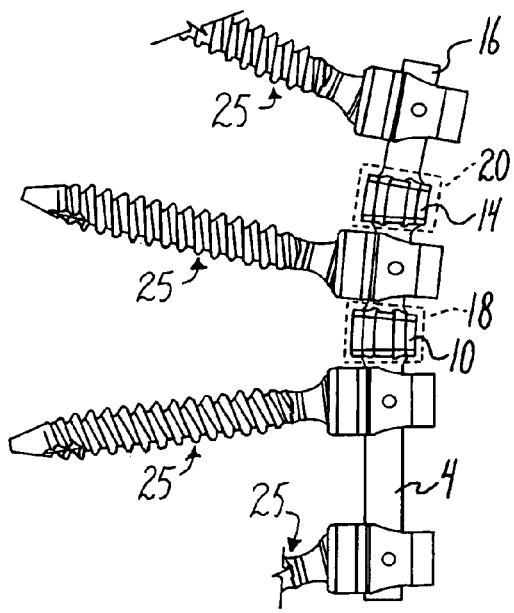
FIG. 18 is a partial side elevational view of the assembly of FIG. 1 with over-molds shown in phantom and the assembly shown operatively responding to spinal extension.
Figure 19:
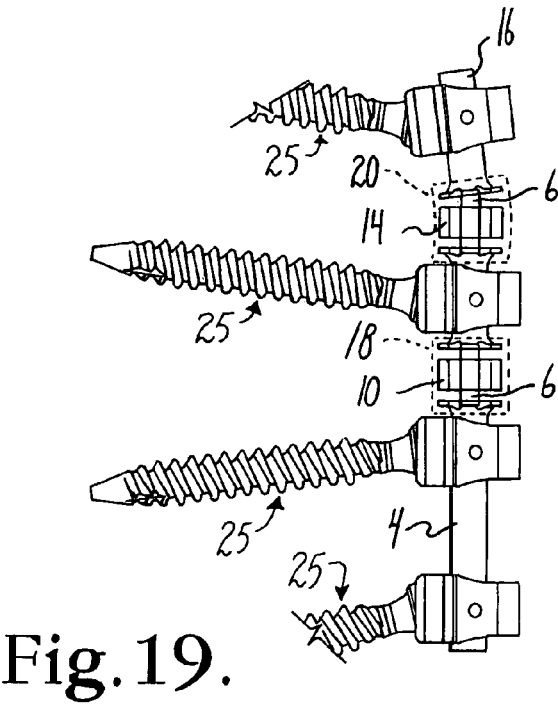
FIG. 19 is a partial side elevational view of the assembly of FIG. 1 with over-molds shown in phantom and the assembly shown operatively responding to a combination of spinal tension and flexion.
Figure 20:
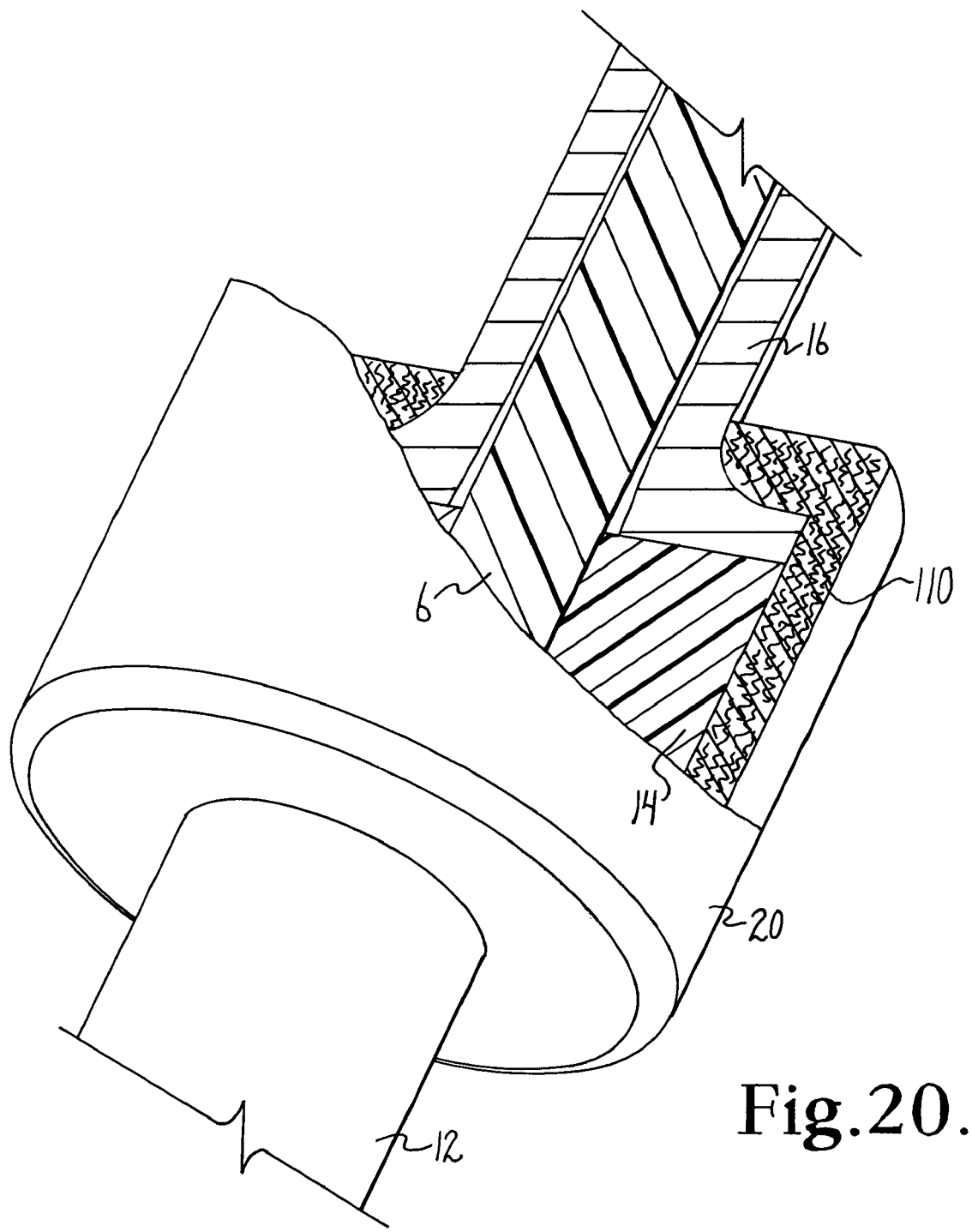
FIG. 20 is an enlarged and partial perspective view of the assembly of FIG. 1 with portions broken away to show the detail thereof and also shown in a neutral state of FIG. 1.

With reference to FIGS. 1 and 32-33, the assembly 1 is illustrated in a neutral position. FIG. 16 illustrates the assembly 1 responding to axial compressive forces. FIG. 17 illustrates the assembly 1 responding to distractive forces, showing how the spacers 10 and 14 are in a neutral position and slidable along the core 6 with the over molds 18 and 20 stretching in response to the movement while covering the assembly 1 and limiting and controlling the sliding movement of the spacers 10 and 14. FIG. 18 illustrates the assembly 1 responding to spinal extension, placing portions of the spacers 10 and 14 in compression and portions of the over molds 18 and 20 in compression and opposed portions thereof stretching in tension. FIG. 19 illustrates the assembly 1 responding to both spinal flexion and tension, spreading the spacers 10 and 14 away from the trolley tube 12 and the anchor members 4 and 16 and along the core 6 with the over molds 18 and 20 stretching in response to the spinal movement. In other embodiments of the invention, the spacer 14 may be made from a material of different durometer than the spacer 10, to allow for a desirable increased upward or cephalad movement, shown by an arrow C, of a portion of the assembly 1.

Eventually, if the spine requires more rigid support, the connecting member assembly 1 according to the invention may be removed and replaced with another longitudinal connecting member, such as a solid rod, having the same outer diameter as the anchor members 4 and 16, utilizing the same bone screw 25 components. Alternatively, if less support is eventually required, a less hard or rigid, more elastic or bendable assembly, for example, an assembly 1 made with elastic spacers of different durometer or geometry may replace the assembly 1, also utilizing the same bone screws 25.

With reference to FIGS. 22-26, an alternative embodiment of a dynamic longitudinal connecting member, generally 201 is substantially similar to the assembly 1 with the exception that it is shorter than the assembly 1 and does not include a trolley tube 12. Thus the assembly 201 cooperates with at least two bone screws 25, one on either side of an elastic and bendable portion thereof. Specifically, the assembly 201 includes a first anchor member 204, an inner floating core 206, an elastic spacer 214 and a second anchor member 216, identical or substantially similar to the anchor member 4, the core 6, the spacer 14 and the anchor member 16 of the assembly 1 previously described herein. The assembly 201 components 204, 206, 214 and 215 are substantially symmetrically aligned with respect to a central axis AA of the assembly 201. The floating core 206 of the anchor member 204 is receivable within the anchor members 204 and 216 and the spacer 214. When assembled with the spacer 214 in contact with the anchor member 204 on one side thereof and the anchor member 216 on an opposed side thereof, an elastic over mold 220 is applied about a buttress plate 240 of the anchor member 204, the spacer 214 and a buttress plate 266 of the anchor member 216. The over mold 220 is identical or substantially similar in form and function to the over mold 20 of the assembly 1 previously described herein.

Figures 22, 23:
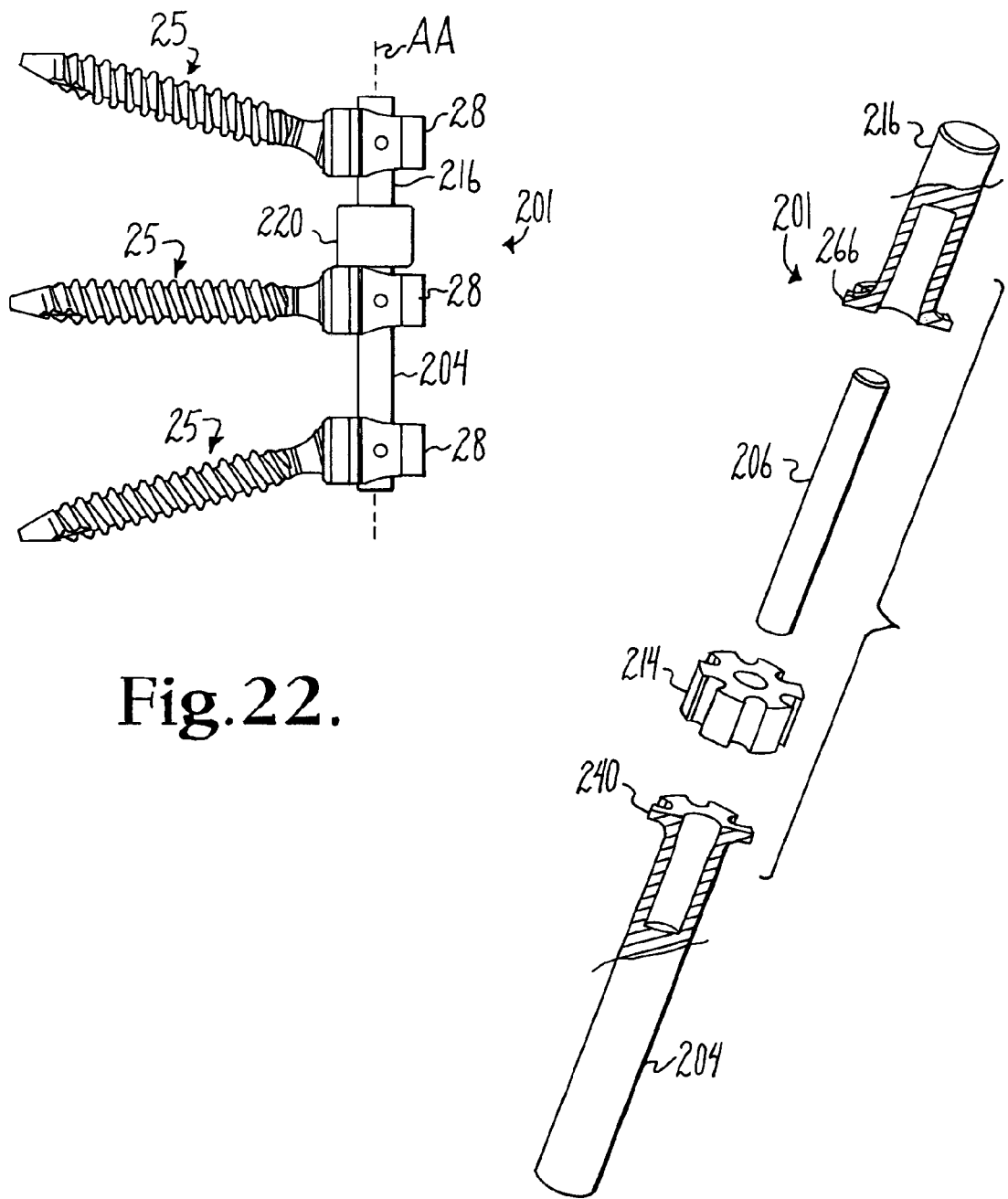
FIG. 22 is a side elevational view of a second embodiment of a dynamic connecting member assembly according to the invention shown with three bone screws.
FIG. 23 is an enlarged and exploded perspective view of the assembly of FIG. 22 with portions broken away to show the detail thereof and prior to addition of an over-mold.

The assembly 201 may then be implanted, cooperating with three bone screws 25 as illustrated in FIG. 22 and as previously described herein with respect to the assembly 1. Unlike the assembly 1 that provides for a more dynamic, bendable and elastic connection between three illustrated bone screws 25, the assembly 201 provides for dynamic stabilization between first and second bone screws 25 and a more rigid and fixed connection between the second bone screw 25 and a third bone screw 25 as both the second and third bone screws are attached to the hard, stiff and inelastic anchor engaging member 204.

Figure 24:
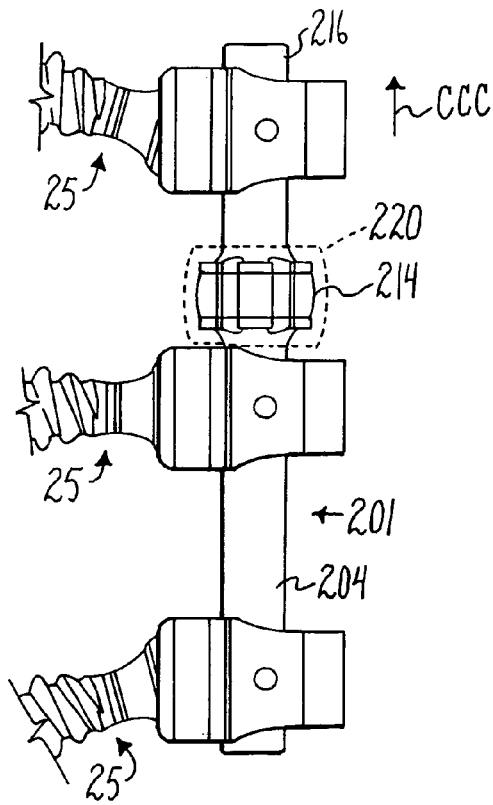
FIG. 24 is an enlarged and partial side elevational view of the assembly of FIG. 22 with the over-mold shown in phantom and spacer shown in compression.
Figure 25:
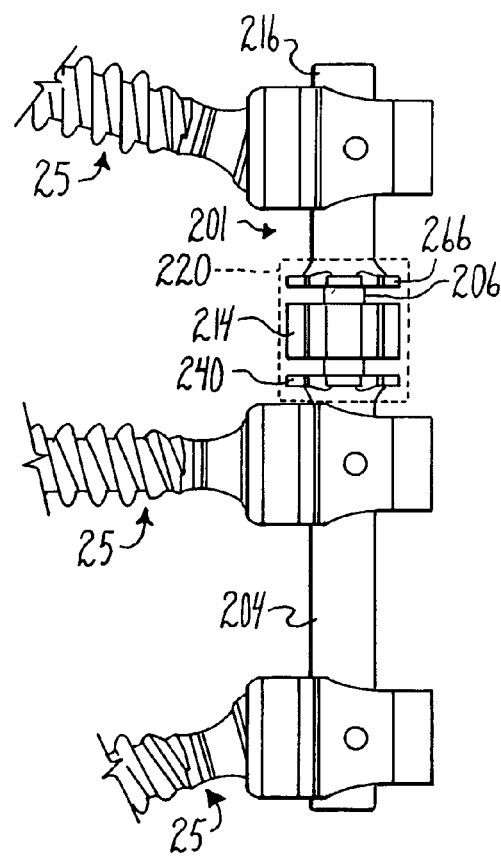
FIG. 25 is an enlarged and partial side elevational view of the assembly of FIG. 22 with the over-mold shown in phantom and the assembly shown expanding in response to tension.
Figure 26:
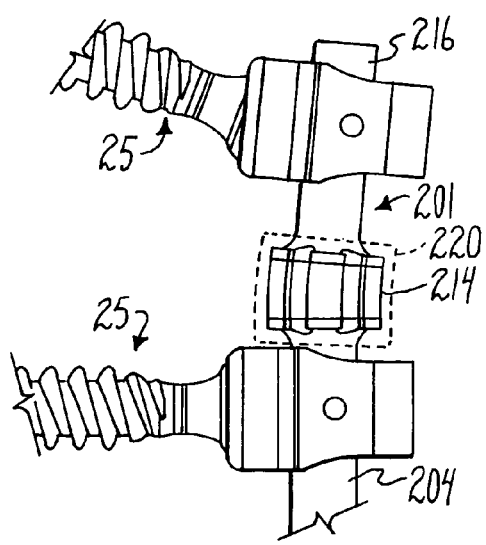
FIG. 26 is an enlarged and partial side elevational view of the assembly of FIG. 22 with the over-mold shown in phantom and the assembly shown operatively responding to spinal extension.

FIGS. 24-26 illustrate a range of bending and axial spinal movement (noted by the arrow CCC) of the assembly 201. FIG. 24 shows both the spacer 214 and the over mold 220 being compressed. FIG. 25 illustrates the assembly 201 responding to distractive forces, showing how the spacer 214 is in a neutral position and slidable along the core 206 with the over mold 220 stretching and straining in response to the tensile stress being applied and limiting and controlling the sliding movement of the spacer 214 and the anchor engaging member 216. The over-mold 220 completely covers the portion of the assembly 201 that is being stretched and tensioned, covering gaps formed between the anchor members 204 and 216 and the compression spacer insert 214, protecting soft tissue along the spine, preventing soft tissue in-growth, holding the assembly 201 together and retaining any wear debris within the assembly 201. FIG. 26 illustrates the assembly 201 in an angulated or bent position as it would be in response to spinal extension, for example, placing portions of the spacer 214 in compression and portions of the over mold 220 in compression and opposed portions thereof stretching in tension.

Figure 27:
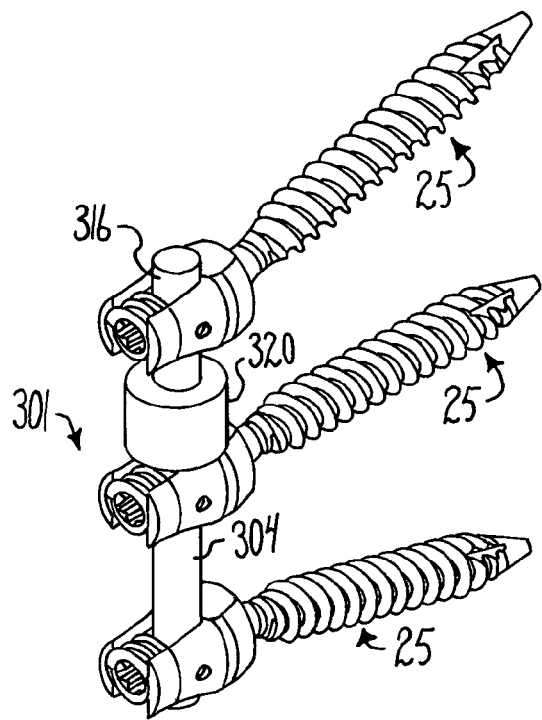
FIG. 27 is a perspective view of a third embodiment of a dynamic connecting member assembly according to the invention shown with three bone screws.
Figure 28:
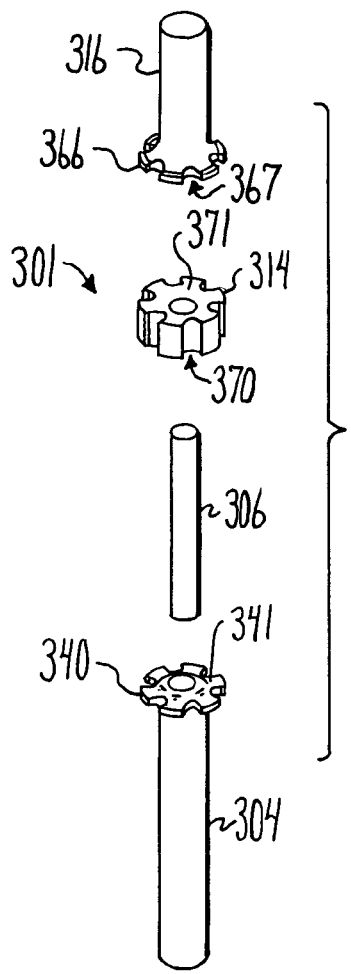
FIG. 28 is an exploded perspective view of the assembly of FIG. 27 shown prior to addition of an over-mold.
Figure 29:
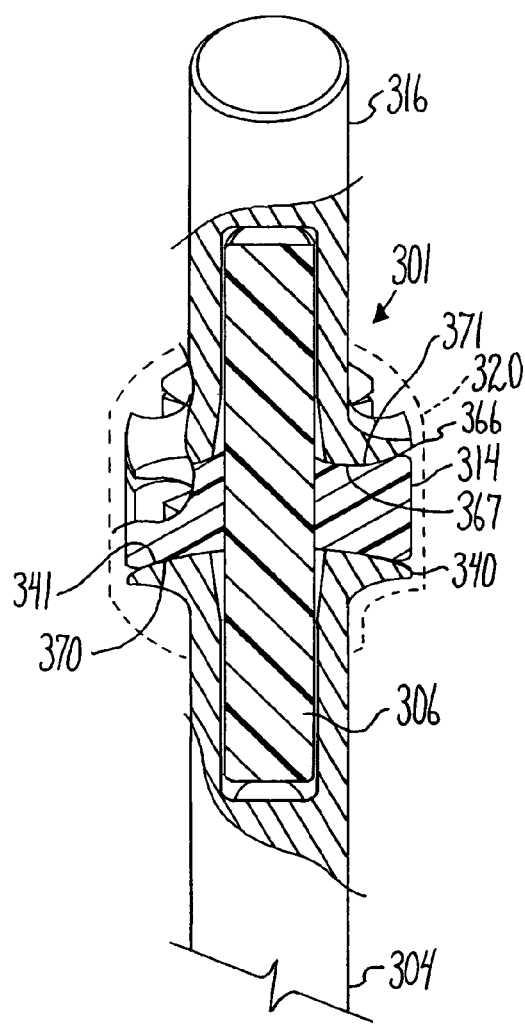
FIG. 29 is an enlarged and partial perspective view of the assembly of FIG. 27 with portions broken away to show the detail thereof and the over-mold shown in phantom.

With reference to FIGS. 27-29, an alternative embodiment of a dynamic longitudinal connecting member, generally 301 is substantially similar to the assembly 201 with the exception of some aspects of the geometry of the anchor engaging members and spacer. Specifically, the assembly 301 includes an anchor member 304, an inner core 306, a compression spacer 314, an anchor member 316 and an over-mold 320 substantially similar in form and function to the respective anchor member 204, core 206, spacer 214, anchor member 216 and over-mold 220 of the assembly 201 previously described herein. The anchor member members 304 and 316 and spacer 314 differ from the respective anchor members 204 and 216 and spacer 214 only with respect to the geometry of the abutment surfaces of such members. As compared to the planar abutment surfaces of the anchor members 204 and 216 and the spacer 214, the anchor member 304 includes a buttress plate 340 that has a convex or domed abutment surface 341 and the anchor member 316 has a buttress plate 366 also having a convex or domed abutment surface 367. The spacer 314 includes opposed abutment surfaces 370 and 371 that are each concave or cupped in shape and are sized and shaped to be closely received by the cooperating buttress plate surfaces 341 and 367. Cooperation between the domed surfaces 341 and 367 and concave surfaces 370 and 371 evens out stresses between the components during bending movement of the assembly 301 and may further allow for limited sliding, articulating movement between the spacer 314 and the anchor members 304 and 316 during bending. The assembly 301 is assembled in a manner substantially similar to the manner of assembly previously described herein with respect to the assemblies 1 and 201. The assembly 301 may then be implanted, cooperating with three bone screws 25 as previously illustrated with respect to the assemblies 1 and 201. Furthermore, the cooperating domed and concave surfaces allow for increased flexion and extension as compared to the assembly 201 having the spacer 214 with planar surfaces.

Figure 30:
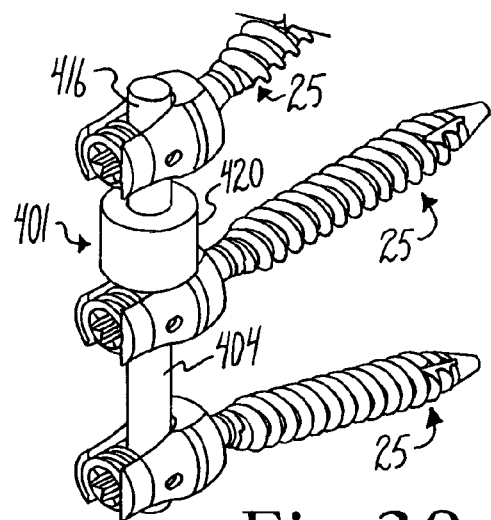
FIG. 30 is a partial perspective view of a fourth embodiment of a dynamic connecting member assembly according to the invention shown with three bone screws.
Figure 31:
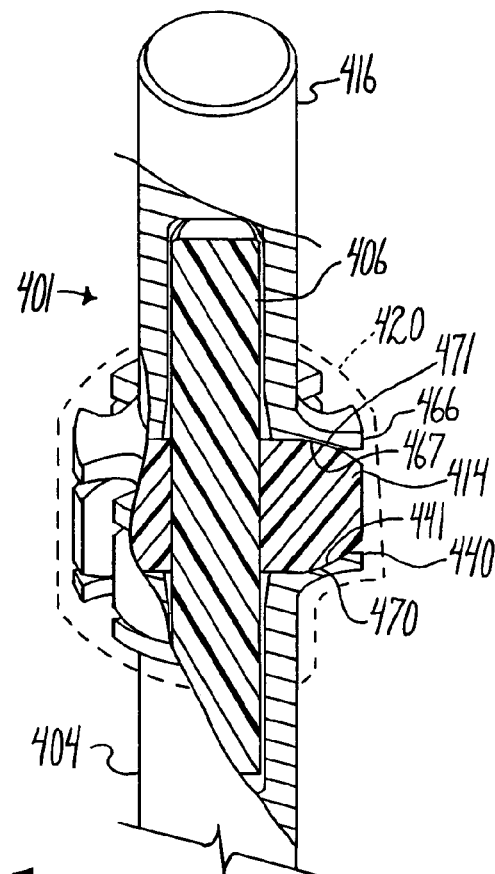
FIG. 31 is an enlarged and partial perspective view of the assembly of FIG. 30 with portions broken away to show the detail thereof and the over-mold shown in phantom.

With reference to FIGS. 30 and 31, another alternative embodiment of a dynamic longitudinal connecting member, generally 401 is substantially similar to the assembly 301 with the exception of the placement of the concave and convex abutment surfaces. Specifically, the assembly 401 includes an anchor engaging member 404, an inner core 406, a compression spacer 414, an anchor engaging member 416 and an over-mold 420 substantially similar in form and function to the respective anchor member 304, core 306, spacer 314, anchor member 316 and over-mold 320 of the assembly 301 previously described herein. However, as compared to the abutment surfaces of the anchor members 304 and 316 and the spacer 314, the anchor member 404 includes a buttress plate 440 that has a concave or cupped abutment surface 441 and the anchor member 416 has a buttress plate 466 also having a concave abutment surface 467. The spacer 414 includes opposed abutment surfaces 470 and 471 that are each convex or domed shaped and sized to be closely received within the cooperating concave buttress plate surfaces 441 and 467. Cooperation between the cupped surfaces 441 and 467 and domed surfaces 470 and 471 evens out stresses between the components during bending movement of the assembly 401 and may further allow for limited sliding, articulating movement between the spacer 414 and the anchor members 404 and 416 during bending of the assembly 401. The assembly 401 is assembled in a manner substantially similar to the manner of assembly previously described herein with respect to the assemblies 1 and 201. The assembly 401 may then be implanted, cooperating with three bone screws 25 as previously illustrated with respect to the assemblies 1 and 201. Furthermore, the cooperating domed and concave surfaces allow for increased flexion and extension as compared to the assembly 201 having the spacer 214 with planar surfaces.

It is to be understood that while certain forms of the present invention have been illustrated and described herein, it is not to be limited to the specific forms or arrangement of parts described and shown.

What is claimed and desired to be secured by Letters Patent is as follows:

1. In a medical implant assembly having at least two bone anchors cooperating with a longitudinal connecting member, the improvement wherein the longitudinal connecting member comprises:
   a) first and second segments, the first segment having a first bore formed in a first end surface thereof, the second segment having a second bore formed in a second end surface thereof, the first segment attached to the first bone anchor and the second segment attached to the second bone anchor;
   b) an inner elongate core partially disposed and slidingly received within each of the bores of the first and second segments;
   c) at least one spacer member disposed about the core and located between the first and second segments; and
   d) an elastic structure surrounding the at least one spacer member, the elastic structure gripping at least the first segment, the spacer member being slidable along the inner core with the elastic structure being in a stretched orientation when one of the first and second segments moves away from the other of the first and second segments.

2. The improvement of claim 1 wherein the elastic structure grips both the first and second segments.

3. The improvement of claim 1 wherein the first segment has a first end plate and the elastic structure is molded about the first end plate.

4. The improvement of claim 1 wherein the spacer member is a first compression spacer and further comprising:
   a) a second elastic compression spacer disposed about the core and located between the first and second segments; and
   b) an inelastic slidable tube, the tube slidably receiving the core, the tube engaging both the first and second compression spacers, the tube attached to a third bone anchor.

5. The improvement of claim 1 wherein the spacer member has opposed parallel end surfaces.

6. The improvement of claim 1 wherein the spacer member has opposed non-parallel load-bearing end surfaces.

7. The improvement of claim 1 wherein the spacer member has a curved load bearing surface.

8. The improvement of claim 1 wherein the first end surface is concave and the spacer member has a convex abutment surface slidably cooperating with the first end surface.

9. The improvement of claim 1 wherein the first end surface is convex and the spacer member as a concave abutment surface slidably cooperating with the first end surface.

10. The improvement of claim 1 wherein the first end surface is planar.

11. The improvement of claim 1 wherein the elastic structure is molded over the at least one spacer member.

12. The improvement of claim 1 wherein the elastic structure is made from a composite material comprising elongate reinforcement strands imbedded in a polymer.

13. The improvement of claim 1 wherein the core is made from a polymer.

14. The improvement of claim 13 wherein the polymer is polyetheretherketone.

15. In a medical implant assembly having at least three bone anchors cooperating with a longitudinal connecting member, the improvement wherein the longitudinal connecting member comprises:
   a) a first inelastic anchor member having a non-integral inner core slidably connected thereto, the inner core being elongate and extending along a substantially central axis of the longitudinal connecting member, the first anchor member being in engagement with at least one of the bone anchors;
   b) at least two elastic compressible spacers, the core being slidingly received in the spacers;
   c) at least one inelastic sleeve located between the spacers, the core being slidingly received within the sleeve, the sleeve being in engagement with at least one of the bone anchors;
   d) a second inelastic anchor member having an aperture for slidingly receiving the inner core; and
   e) first and second elastic over-molds, the first over-mold surrounding the first spacer and the second over-mold surrounding the second spacer, the first over-mold attaching the first anchor member to the sleeve, the second over-mold attaching the second anchor member to the sleeve.

16. The improvement of claim 15 wherein the at least one sleeve has an inner surface defining a through bore, the core being received in the through bore and in sliding relation with the sleeve inner surface, the sleeve inner surface being non-linear in cross-section taken along the central axis, the surface flaring radially outwardly towards at least one of the first and second spacers.

17. The improvement of claim 16 wherein the sleeve inner surface is hyperboloid.

18. In a medical implant assembly having at least two bone anchors cooperating with a longitudinal connecting member, the improvement wherein the longitudinal connecting member comprises:
   a) an anchor member having an inner aperture slidingly receiving a discrete inner core, the core extending from the anchor member along a central axis of the connecting member, the core being surrounded by a remainder of the connecting member and in one of spaced and slidable relation thereto;
   b) at least one elastic spacer, the core being slidingly received in the spacer along the axis, the spacer being positioned between the at least two bone anchors;
   c) at least one inelastic sleeve, the core being slidingly received within the sleeve along the axis, the sleeve being in engagement with at least one of the bone anchors; and
   d) an over-molded elastomer surrounding the spacer and attached to the anchor member and the sleeve.

19. The improvement of claim 18 wherein the elastic spacer is in compression and the over-molded elastomer is in tension prior to implantation.

20. The improvement of claim 18 wherein the over-molded elastomer further comprises reinforcement strands.

21. The improvement of claim 20 wherein the reinforcement strands are sinusoidal.

22. In a medical implant assembly having at least two bone attachment structures cooperating with a longitudinal connecting member, the improvement wherein the longitudinal connecting member comprises:
   a) an anchor member having a first width and an aperture;
   b) a discrete core having a second smaller width, the core slidingly received in the aperture and freely movable along a central axis of the connecting member, the first and second widths measured in a direction perpendicular to the axis;
   c) at least one elastic outer spacer, the core being slidingly received in the spacer along the axis, the spacer being positioned between the at least two bone attachment structures;
   d) at least one inelastic sleeve, the core being slidingly received within the sleeve along the axis, the sleeve being in engagement with at least one of the bone attachment structures, the sleeve having an inner surface defining a through bore for receiving the core, at least a portion of the inner surface being non-linear in a cross-section taken along the axis; and
   e) at least one over-molded elastomeric covering, the covering in contact with the anchor member, the spacer and the sleeve.

23. The improvement of claim 22 wherein the sleeve inner surface flares radially outwardly in a direction toward the at least one compressible outer spacer.

24. The improvement of claim 22 wherein the sleeve inner surface is hyperboloid in shape.

25. The improvement of claim 22 wherein the spacer is pre-compressed.

26. The improvement of claim 22 wherein the covering further comprises elongate reinforcement strands imbedded in a polymer.

27. In a medical implant assembly having at least two bone anchors cooperating with a longitudinal connecting member, the improvement wherein the longitudinal connecting member comprises:
   a) an anchor member having a closed ended central inner aperture slidingly receiving and encircling a discrete inelastic inner core, the core extending from the anchor member along a central axis of the connecting member, the core being surrounded by a remainder of the connecting member and in one of spaced and slidable relation thereto;
   b) at least one spacer having a spacer bore, the core being slidingly received in the spacer bore along the axis, the spacer being positioned between the at least two bone anchors; and
   c) at least one inelastic sleeve trolley tube having a central trolley tube bore, the core being slidingly received within the trolley tube bore along the axis, the trolley tube being in engagement with at least one of the bone anchors.

28. In a medical implant assembly having at least two bone attachment structures cooperating with a longitudinal connecting member, the improvement wherein the longitudinal connecting member comprises:
   a) an anchor member having a first width and a closed ended inner central aperture;
   b) a discrete inelastic core having a second smaller width, the core slidingly being received in and fully encircled by the anchor member aperture and freely movable along a central axis of the connecting member, the first and second widths measured in a direction perpendicular to the axis;
   c) at least one outer spacer having a spacer bore, the core being slidingly received in the spacer bore along the axis, the spacer being positioned between the at least two bone anchors; and
   d) at least one inelastic tube trolley having a central tube bore, the core being slidingly received within the tube bore along the axis, the tube being in engagement with at least one of the bone attachment structures, the sleeve having an inner surface defining a through bore for receiving the core, at least a portion of the tube inner surface being non-linear in a cross-section taken along the axis.

* * * * *